(12) United States Patent
Myers et al.

(10) Patent No.: US 11,654,163 B2
(45) Date of Patent: May 23, 2023

(54) LIPID COMBINATIONS

(71) Applicant: PHARMALINK INTERNATIONAL LIMITED, Hong Kong (CN)

(72) Inventors: Stephen Myers, Evans Head (AU); Christopher Oliver, Tregeagle (AU)

(73) Assignee: PHARMALINK INTERNATIONAL LIMITED, Hong Kong (CN)

( * ) Notice: Subject to any disclaimer, the term of this patent is extended or adjusted under 35 U.S.C. 154(b) by 0 days.

(21) Appl. No.: 16/481,444

(22) PCT Filed: Dec. 21, 2018

(86) PCT No.: PCT/IB2018/060482
§ 371 (c)(1),
(2) Date: Jul. 26, 2019

(87) PCT Pub. No.: WO2019/123400
PCT Pub. Date: Jun. 27, 2019

(65) Prior Publication Data
US 2020/0093867 A1      Mar. 26, 2020

(30) Foreign Application Priority Data

Dec. 22, 2017   (AU) ............................... 2017905181

(51) Int. Cl.
*A61K 35/618* (2015.01)
*A61K 9/48* (2006.01)
(Continued)

(52) U.S. Cl.
CPC .............. *A61K 35/618* (2013.01); *A61K 9/48* (2013.01); *A61K 35/612* (2013.01); *A61P 29/00* (2018.01); *C11B 1/10* (2013.01)

(58) Field of Classification Search
CPC ...... A61K 35/618; A61K 9/48; A61K 35/612; A61K 31/355; A61K 9/4858; A61K 2300/00; A61P 29/00; C11B 1/10
See application file for complete search history.

(56) References Cited

U.S. PATENT DOCUMENTS 6,800,299 B1    10/2004    Beaudoin et al.
8,383,845 B2    2/2013     Catchpole et al.
(Continued)

FOREIGN PATENT DOCUMENTS

AU      2013227998 A1    9/2013
CN         1351471 A     5/2002
(Continued)

OTHER PUBLICATIONS

Myers et al, Comment on "Effects of different omega-3 sources, fish oil, krill oil, and green-lipped mussel against cytokine-mediated canine cartilage degradation" In Vitro Cell Dev Biol Anim. 2017, https://link.springer.com/article/10.1007/s11626-017-0188-4, pp. 1-5. (Year: 2017).*

(Continued)

*Primary Examiner* — Trevor Love
(74) *Attorney, Agent, or Firm* — Seed Intellectual Property Law Group LLP

(57) ABSTRACT

A combination or composition of mussel lipid and krill oil is disclosed, which is used to treat inflammation or pain. A process for preparing hill oil having a phospholipid content of about 50% or greater is also disclosed.

21 Claims, 24 Drawing Sheets

Figure 1A:
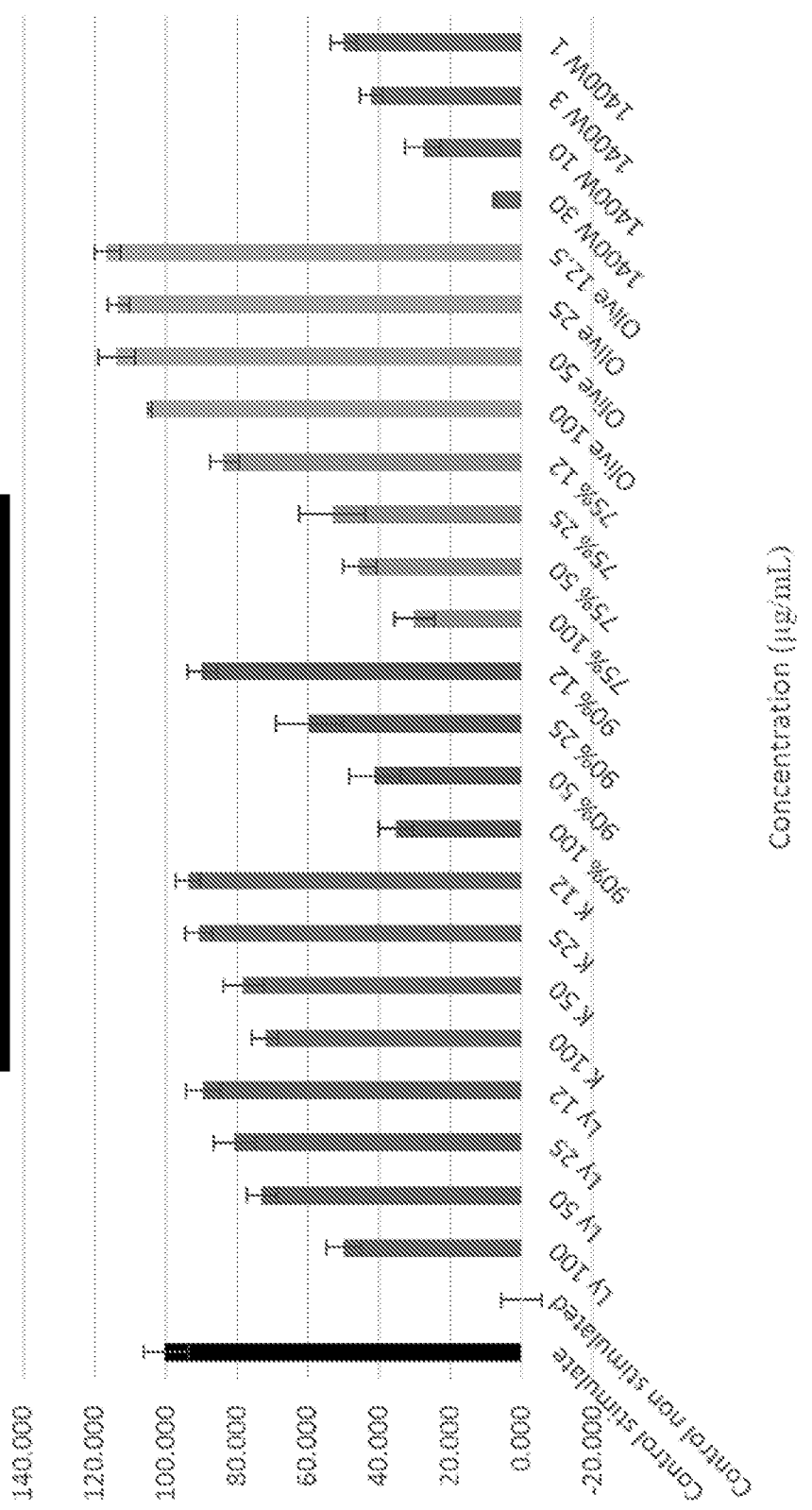

(51) Int. Cl.
  *A61K 35/612* (2015.01)
  *A61P 29/00* (2006.01)
  *C11B 1/10* (2006.01)

(56) References Cited

U.S. PATENT DOCUMENTS

| | | | |
|---|---|---|---|
| 8,828,447 | B2 | 9/2014 | Soerensen et al. |
| 9,028,877 | B2 | 5/2015 | Bruheim et al. |
| 9,150,815 | B2 | 10/2015 | Sclabos Katevas et al. |
| 9,375,453 | B2 | 6/2016 | Bruheim et al. |
| 2008/0234362 | A1 | 9/2008 | Chandler |
| 2011/0020316 | A1 | 1/2011 | Minatelli et al. |
| 2012/0231087 | A1 | 9/2012 | Bruheim et al. |
| 2015/0224149 | A1 | 8/2015 | Solovyev |
| 2017/0281689 | A1 | 10/2017 | Bettle, III |

FOREIGN PATENT DOCUMENTS

| | | |
|---|---|---|
| CN | 105685482 A | 6/2016 |
| CN | 106306554 A | 1/2017 |
| EP | 2 612 672 A1 | 7/2013 |
| JP | H11512400 A | 10/1999 |
| JP | 2004534800 A | 11/2004 |
| JP | 2013508431 A | 3/2013 |
| JP | 5215858 B2 | 6/2013 |
| JP | 2015504947 A | 2/2015 |
| WO | WO 9709992 A1 | 3/1997 |
| WO | WO 02102394 A2 | 12/2002 |
| WO | WO 2005073354 A1 | 8/2005 |
| WO | WO 2006128244 A1 | 12/2006 |
| WO | 2007/123424 A1 | 11/2007 |
| WO | WO 2007123424 A1 | 11/2007 |
| WO | WO 2008035756 A1 | 3/2008 |
| WO | WO 2011050474 A1 | 5/2011 |
| WO | 2012/012372 A1 | 1/2012 |
| WO | 2012/037328 A2 | 3/2012 |
| WO | 2013/052587 A2 | 4/2013 |
| WO | WO 2013102792 A2 | 7/2013 |
| WO | WO 2015104401 A1 | 7/2015 |
| WO | WO 2015121378 A1 | 8/2015 |
| WO | 2015/142705 A1 | 9/2015 |
| WO | 2019/111055 A1 | 6/2019 |

OTHER PUBLICATIONS

Li et al, The absorption kinetics of Antarctic krill oil phospholipid liposome in blood and the digestive tract of healthy mice by single gavage, 2020, Food Science and Human Wellness, 9, 88-94. (Year: 2020).*

Interpharma, Pure Krill Oil, https://www.interpharma.co.th/en/interpharma-en/wellness-en-2/new-generation-omega3-e, Accessed 2021, pp. 1-17. (Year: 2021).*

"Nature's Own Green Lipped Mussel + Krill 84 Caps," URL= https://www.catch.com.au/product/nature-s-own-green-lipped-mussel-krill-84-caps-339265/, download date Sep. 28, 2020, 3 pages.

Buddhachat et al., "Effects of different omega-3 sources, fish oil, krill oil, and green-lipped mussel against cytokine-mediated canine cartilage degradation," *In Vitro Cell. Dev. Biol.—Animal* 53:448-457, 2017.

Deutsch, "Evaluation of the Effects of Neptune Krill Oil on Chronic Inflammation and Arthritic Symptoms," *Journal of the American College of Nutrition* 26(1):39-48, 2007.

Gibson et al., "The treatment of arthritis with a lipid extract of *Perna canaliculus*: a randomized trial," *Complementary Therapies in Medicine* 6:122-126, 1998.

Gimbom, "Gim Dog® Little Darling: Mobility Snack Paste," Mintel, Record ID: 3645015, Dec. 2015, URL=<https://www.gnpd.com/sinatra/recordpage/3645015, 6 pages.

Ierna et al., "Supplementation of diet with krill oil protects against experimental rheumatoid arthritis," *BMC Musculoskeletal Disorders* 11(136):1-11, 2010.

Lau et al., "Treatment of knee osteoarthritis with Lyprinol®, lipid extract of the green-lipped mussel—a double-blind placebo-controlled study," *Progress in Nutrition* 6(1):17-31, 2004.

Natural Medicines Patient Handout, "Krill Oil," Consumer Information and Education, Sep. 6, 2019, URL=https://naturalmedicines.therapeuticresearch.com/databases/food,-herbs-supplements/patienthandout.aspx?productid=1172&lang=en, download date Sep. 21, 2020, 4 pages.

Natural Medicines Patient Handout, "New Zealand Green-Lipped Mussel," Consumer Information and Education, Mar. 31, 2020, URL=https://naturalmedicines.therapeuticresearch.com/databases/food,-herbs-supplements/patienthandout.aspx?productid=830&lang=en, download date Sep. 21, 2020, 2 pages.

Nichols et al., "Recent Advances in Omega-3: Health Benefits, Sources, Products and Bioavailability," *Nutrients* 6:3727-3733, 2014.

Rialland et al., "Effect of a diet enriched with green-lipped mussel on pain behavior and functioning in dogs with clinical osteoarthritis," *The Canadian Journal of Veterinary Research* 77:66-74, 2013.

Siriwardhana et al., "Health Benefits of n-3 Polyunsaturated Fatty Acids: Eicosapentaenoic Acid and Docosahexaenoic Acid," *Advances in Food and Nutrition Research* 65:211-222, 2012. (abstract only).

He et al., "Health Benefits of Antarctic Krill oil," *Food Research and Development* 34(20):130-133, 2013.

Liu, "Research on Supercritical CO2 extraction process of krill oil from wet Antarctic krill (*Euphausia superb*)," master's thesis, Ocean University of China, 2015. (9 pages) (w/ English Abstract).

Whitehouse et al., "Anti-inflammatory activity of a lipid fraction (lyprinol) from the NZ green-lipped mussel," *Inflammophaarmacology* 5:231-246, 1997. (8 pages).

Zawadzki et al., "*Perna canaliculus* Lipid Complex PCSO-524™ Demonstrated Pain Relief for Osteoarthritis Patients Benchmarked against Fish Oil, a Randomized Trial, without Placebo Control," *Mar. Drugs* 11:1920-1935, 2013.

"GlycOmega™ Oil: Greenshell™ Mussell Oil," © Aroma New Zealand Ltd, Sep. 1998, 2 pages.

"PemaTec™ Greenshell Mussell Oil Extract," Waitaki Biosciences, as early as Apr. 2017, 4 pages.

Miller, M.R., et al., "Detailed Distribution of Lipids in Greenshell™ Mussel (*Perna canaliculus*)," *Nutrients* 6:1454-1474, 2014.

Murphy, K.J., et al., "Fatty Acid and Sterol Composition of Frozen and Freeze-Dried New Zealand Green Lipped Mussel (*Perna canaliculus*) From Three Sites in New Zealand," *Asia Pacific J. Clin Nutr* 12(1):50-60, 2003.

Sinclair, A.-J., et al., "Marine Lipids: Overview 'News Insights and Lipid Composition of Lyprinol™,'" *Allergie et Immunologie* 32(7):261-271, 2000.

"History of Changes for Study: NCT03760757 Effectiveness of Two Different Forms of Marine Oil on Indirect Markers of Muscle Damage and Soreness in Untrained Men," ClinicalTrials.gov Archive, Nov. 29, 2018 (6 pages).

"History of Changes for Study: NCT03760757 Effectiveness of Two Different Forms of Marine Oil on Indirect Markers of Muscle Damage and Soreness in Untrained Men," ClinicalTrials.gov Archive, Dec. 17, 2018 (6 pages).

"Krill Oil Monograph," *Alternative Medicine Review* 15(1):84-86, 2010.

Banni et al., "Krill oil significantly decreases 2-arachidonoylglycerol plasma levels in obese subjects," *Nutrition & Metabolism* 8:7, 2011. (6 pages).

Bunea et al., "Evaluation of the Effects of Neptune Krill Oil on the Clinical Course of Hyperlipidemia," *Altern Med Rev* 9(4):420-428, 2004.

Burri, "Krill Oil: The Power of 4," AkerBioMarine, Krill Phospholipid Omega-3s—Healthy Cells, Healthy Tissues, Healthy Body, 2013. (12 pages.).

Calder, "Omega-3 Fatty Acids and Inflammatory Processes," *Nutrients* 2:355-374, 2010.

Doggrell, "Lyprinol—Is It a Useful Anti-Inflammatory Agent?" *Evidence-Based Complementary and Alternative Medicine* 2011:307121, 2011. (7 pages).

(56) References Cited

OTHER PUBLICATIONS

Eason et al., "Greenshell™ Mussels: A Review of Veterinary Trials and Future Research Directions," *Veterinary Sciences* 5:36, Mar. 27, 2018. (9 pages).

Gibson et al., "*Perna canaliculus* in the treatment of arthritis," *Clinical Trials* 224:955-960, Sep. 1980.

Gibson et al., "Seatone in arthritis," *British Medical Journal* 282:1795, May 30, 1981.

Gigliotti et al., "Extraction and characterisation of lipids from Antarctic krill (*Euphausia superba*)," *Food Chemistry* 125:1028-1036, 2011.

Gil et al., "Systematic reviews of the role of omega-3 fatty acids in the prevention and treatment of disease," *British Journal of Nutrition* 107:S1-S2, 2012.

Hagen et al., "Lipid metabolism of the Antarctic krill *Euphausia superba* and its ecological implications," *Marine Biology* 139:95-104, 2001.

Hielm-Björkman et al., "Evaluating Complementary Therapies for Canine Osteoarthritis Part I: Green-lipped Mussel (*Perna canaliculus*)," *eCAM* 6(3):365-313, 2009.

Jacobs, "CO2 Marine Lipid Extract from Green Lipped Mussel Oil: Introductory Information about Marine Lipids Extracted From *Perna canaliculus*," Lyprinol™, Aug. 2009. (15 pages).

Lee et al., "Pain Controlling and Cytokine-regulating Effects of Lyprinol, a Lipid Extract of *Perna Canaliculus*, in a Rat Adjuvant-induced Arthritis Model," *eCAM* 6(2):239-245, 2009.

Mickleborough et al., "The effects PCSO-524®, a patented marine oil lipid and omega-3 PUFA blend derived from the New Zealand green lipped mussel (*Perna canaliculus*), on indirect markers of muscle damage and inflammation after muscle damaging exercise in untrained men: a randomized, placebo controlled trial," *Journal of the International Society of Sports Nutrition* 12:10, 2015. (17 pages).

Miller et al., "Changes in proximate composition, lipid class and fatty acid profile in Greenshell™ mussels (*Perna canaliculus*) over an annual cycle," *Aquaculture Research* 49(3):1153-1165, first available online Dec. 1, 2017.

Rangel-Huerta et al., "Omega-3 long-chain polyunsaturated fatty acids supplementation on inflammatory biomakers: a systematic review of randomised clinical trials," *British Journal of Nutrition* 107:S159-S170, 2012.

Sampalis et al., "Evaluation of the Effects of Neptune Krill Oil™ on the Management of Premenstrual Syndrome and Dysmenorrhea," *Altern Med Rev* 8(2):171-179, 2003.

Szechiński et al., "Measurement of pain relief resulting from the administration of *Perna canaliculus* lipid complex PCSO-524™ as compared to fish oil for treating patients who suffer from osteoarthritis of knee and/or hip joints," *Reumatologia* 49(4):244-252, 2011.

Treschow et al., "Novel anti-inflammatory ω-3 PUFAs from the New Zealand green-lipped mussel, *Perna canaliculus*," *Comparative Biochemistry and Physiology, Part B* 147:645-656, 2007.

Virtue et al., "Changes in the digestive gland of *Euphausia superba* during short-term starvation: lipid class, fatty acid and sterol content and composition," *Marine Biology* 117:441-448, 1993.

Virtue et al., "Reproductive trade-off in male Antarctic krill, *Euphausia superba*," *Marine Biology* 126:521-521, 1996.

Virtue et al., "The lipid composition of *Euphausia superba* Dana in relation to the nutritional value of *Phaeocystis pouchetil* (Harlot) Lagerhelm," *Antarctic Science* 5(2):169-177, 1993.

Winther et al., "Elucidation of Phosphatidylcholine Composition in Krill Oil Extracted from *Euphausia superba*," *Lipids* 46:25-36, 2011.

Yashodhara et al., "Omega-3 fatty acids: a comparative review of their role in health and disease," *Postgrad Med J* 85:84-90, 2009.

Radiance™, "OsteoFlex," URL=https://web.archive.org/web/20180130003816/http://radiance.co.nz/product/osteoflex/, webpage retrieved from The Wayback Machine, dated Jan. 30, 2018, (2 pages).

\* cited by examiner

LIPID COMBINATIONS

FIELD

The present disclosure relates generally to combinations of marine lipids. In particular the disclosure relates to a combination of lipids obtained from *Perna canaliculus* and krill, compositions and preparations comprising said combinations and the use of said combinations and compositions in therapy. The disclosure further relates to processes for the manufacture of krill oils and their use in the combinations and compositions.

BACKGROUND

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Inflammation is a necessary physiological adaptive response to injury and infection, without which humans and animals could not survive. Its function is to eliminate the initial cause of injury, remove offending factors and initiate repair of tissue structure and function. Its early acute phase is typically characterised by heat, pain, redness and swelling. The usual outcome of acute inflammation is restoration and repair of damage, however, disproportionate acute and longer-term chronic inflammatory responses in conditions such sepsis can be harmful.

Importantly, chronic inflammation has now been implicated in the pathology of a wide number of diseases affecting all tissues and organs including osteoarthritis, rheumatoid arthritis, cardiovascular disease, cerebrovascular disease, respiratory disease, autoimmune disease and sarcopenia; indeed chronic inflammation has been implicated in the process of ageing itself.

As a response to the inflammatory process, there has been the development of a range of drugs, the most effective being glucocorticoid steroid drugs which are capable of suppressing excessive inflammation. However, steroid drug therapy is limited in its widespread clinical use due to significant side-effects, and is generally restricted to short-term use only. A second class of inflammatory drugs was developed called the non-steroidal anti-inflammatory drugs (NSAIDS) such as ibuprofen etc see Table 1. It was recognised that aspirin had anti-inflammatory activity and that it was part of this second class of anti-inflammatory drugs. These drugs were safer than steroid drugs and could be used for more chronic inflammatory conditions, such as osteoarthritis.

TABLE 1

| \multicolumn{2}{l}{List of commonly used non-steroidal anti-inflammatory drugs (NSAIDS)} |  |
| --- | --- |
| Generic name | Brand name(s) |
| celecoxib | Celebrex |
| diclofenac | Cambia, Cataflam, Dyloject, Flector, Pennsaid, Solaraze, Voltaren, Voltaren-XR, Zipsor, Zorvolex, Arthrotec (combination with misoprostol) |
| diflunisal | No brand name currently marketed |
| etodolac | No brand name currently marketed |
| fenoprofen | Nalfon |
| flurbiprofen | Ansaid |
| ibuprofen | Advil, Caldolor, Children's Advil, Children's Elixsure IB, Children's Motrin, Ibu-Tab, Ibuprohm, Motrin IB, Motrin Migraine Pain, Profen, Tab-Profen, Duexis (combination with famotidine), Reprexain (combination with hydrocodone), Vicoprofen (combination with hydrocodone) |
| indomethacin | Indocin, Tivorbex |
| ketoprofen | No brand name currently marketed |
| ketorolac | Sprix |
| mefenamic acid | Ponstel |
| meloxicam | Mobic |
| nabumetone | No brand name currently marketed |
| naproxen | Aleve, Anaprox, Anaprox DS, EC-Naprosyn, Naprelan, Naprosyn, Treximet (combination with sumatriptan), Vimovo (combination with esomeprazole) |
| oxaprozin | Daypro |
| piroxicam | Feldene |
| sulindac | Clinoril |
| tolmetin | No brand name currently marketed |

Prostaglandins play a key role in the inflammatory response, with their presence significantly increased in inflamed tissue, contributing to pain and fever by raising temperature, and dilating blood vessels, which causes redness and swelling in the place they are released. NSAIDs are competitive site inhibitors of both cyclooxygenase-1 (COX-1) and cyclooxygenase-2 (COX-2), and thereby reduce the synthesis of prostaglandins. By reducing production of prostaglandins NSAIDs help relieve the discomfort of fever and reduce inflammation and the associated pain. NSAIDS are usually used for the treatment of acute and chronic conditions characterised by pain and inflammation, such as osteoarthritis, rheumatoid arthritis, headache and migraine, and fever. However, NSAIDS also present considerable issues around safety, and can exhibit gastrointestinal, renal and cardiovascular toxicities. For example, aspirin can cause gastric bleeding within several days of use and in July 2015, the FDA repeated a previous warning about the heart hazards of common NSAID pain relievers, excluding aspirin. These include ibuprofen (Advil, Motrin) and naproxen (Aleve) and prescription-only NSAIDs.

Accordingly, there is a need for further alternative anti-inflammatory therapies.

SUMMARY

It has now been found that certain combinations of mussel lipid and krill oil may advantageously provide an additive or synergistic inhibitory effect against the production or release of one or more pro-inflammatory mediators implicated in the inflammatory process. In some embodiments, combinations of the present disclosure may therefore afford new therapeutic treatments for disorders characterised by inflammation, or having an inflammatory component. In some embodiments, combinations of the present disclosure may afford new therapeutic treatments for pain, such as pain associated with inflammation.

Thus, in one aspect, there is provided a combination comprising mussel lipid and krill oil. The mussel lipid and krill oil combination may be adapted for separate or simultaneous administration to a subject. In some embodiments, the combination is a composition comprising mussel lipid and a krill oil.

In another aspect, there is provided a combination consisting, or consisting essentially, of mussel lipid and krill oil. The mussel lipid and krill oil combination may be adapted for separate or simultaneous administration to a subject. In some embodiments, the combination is a composition consisting, or consisting essentially of mussel lipid and a krill oil.

In another aspect there is provided a combination comprising mussel lipid and krill oil for use in therapy. In some embodiments, there is provided a combination comprising mussel lipid and krill oil for use in treating inflammation in a subject. There is also provided a combination comprising mussel lipid and krill oil for use in treating pain in a subject. The mussel lipid and krill oil combination may be adapted for separate or simultaneous administration to a subject. In some embodiments, the combination is a composition comprising mussel lipid and a krill oil.

In another aspect, the disclosure provides a method of treating inflammation in a subject in need thereof, comprising administering to said subject a combination comprising mussel lipid and krill oil. The disclosure also provides a method of treating pain in a subject in need thereof, comprising administering to said subject a combination comprising mussel lipid and krill oil. The mussel lipid and krill oil combination may be adapted for separate or simultaneous administration to a subject. In some embodiments, the combination is a composition comprising mussel lipid and a krill oil.

In another aspect, the disclosure provides use of mussel lipid and krill oil in the manufacture of a combination medicament for treating inflammation. The disclosure also provides use of mussel lipid and krill oil in the manufacture of a combination medicament for treating pain. The medicament may be adapted for separate or simultaneous administration. In some embodiments, the combination is a composition comprising mussel lipid and a krill oil.

In another aspect, the disclosure provides a combination agent for treating inflammation, said combination comprising mussel lipid and krill oil. The disclosure also provides a combination agent for treating pain, said combination comprising mussel lipid and krill oil. The mussel lipid and krill oil may be adapted for separate or simultaneous administration to a subject. In some embodiments, the combination agent is a composition comprising mussel lipid and a krill oil.

In some embodiments, the mussel lipid is in the form of a dried mussel powder. In other embodiments, the mussel lipid is in the form of a lipid extract obtained from mussel ("mussel lipid extract"). In still further embodiments, the mussel lipid may be in the form of a combination or composition of dried mussel powder and mussel lipid extract.

In some embodiments, the krill oil has a phospholipid content in the range of about 40-99% w/w, and in further embodiments a phospholipid content in the range of about 50-99% w/w, such as about 60-80% w/w.

In some embodiments, the combinations of the disclosure may be useful in treating one or more disorders in a subject, wherein the disorder has an inflammatory component, and whereby the inhibition of one or more pro inflammatory molecules is therapeutically beneficial. In some embodiments, the combinations may be suitable for treating one or more chronic disorders.

In some embodiments, such as for use in treating chronic inflammation, the combinations may eliminate, avoid or otherwise mitigate the extent, severity or duration of one or more adverse effects associated with commonly available NSAIDS.

In another aspect, there is provided a process for preparing krill oil having a phospholipid content of about 50% or greater, such as about 60% or greater, comprising the steps of:

(a) contacting a krill biomass feed material with a mixture of $CO_2$ and ethanol, to extract a krill oil; and (b) contacting said krill oil with $CO_2$ to extract at least a proportion of non-polar lipid components such that the oil has a phospholipid content of at least 50% w/w.

In some embodiments, the krill oil obtained from this process has a phospholipid content of about 60% w/w or greater, such as at least about 65% w/w, or 70% w/w, or 75% w/w, or 80% w/w, or 85% w/w, or 90% w/w.

The disclosure also relates to processes for enriching the phospholipid content of a krill oil.

Thus, in a further aspect, there is provided a process for increasing the phospholipid content of a krill oil having a phospholipid content of less than 50% w/w to about 50% w/w or greater, comprising the step of contacting a krill oil having a phospholipid content of less than 50% w/w with $CO_2$ to selectively remove non-polar lipid components.

In some embodiments, the preliminary krill oil has a phospholipid content of less than about 50%, w/w, such as less than about 40%, or less than about 30% w/w or 20% w/w. In some embodiments, the enriched oil so obtained has a phospholipid content of at least about 55% w/w, or at least about 60% w/w, or at least about 65% w/w or at least about 70% w/w or at least about 75% w/w or at least about 80% w/w or at least about 85% w/w or at least about 90% w/w.

A further embodiment provides krill oil having a phospholipid content of about 50% w/w or greater, (e.g. ≥60% w/w) obtained by a process of the disclosure.

Still further embodiments provide krill oil having a phospholipid content of about 50% or 60% w/w or greater for use in the combinations and compositions described herein.

FIGURES

FIG. 1A graphically depicts the NO inhibition effect in lipopolysaccharide (LPS) and interferon γ (IFγ) stimulated RAW264.7 cells for various concentrations of combinations of mussel lipid extract and krill oil, each of mussel lipid extract and krill oil alone, olive oil and N-(3-(Aminomethyl) benzyl)acetamidine (1400W).

Figure 1B:
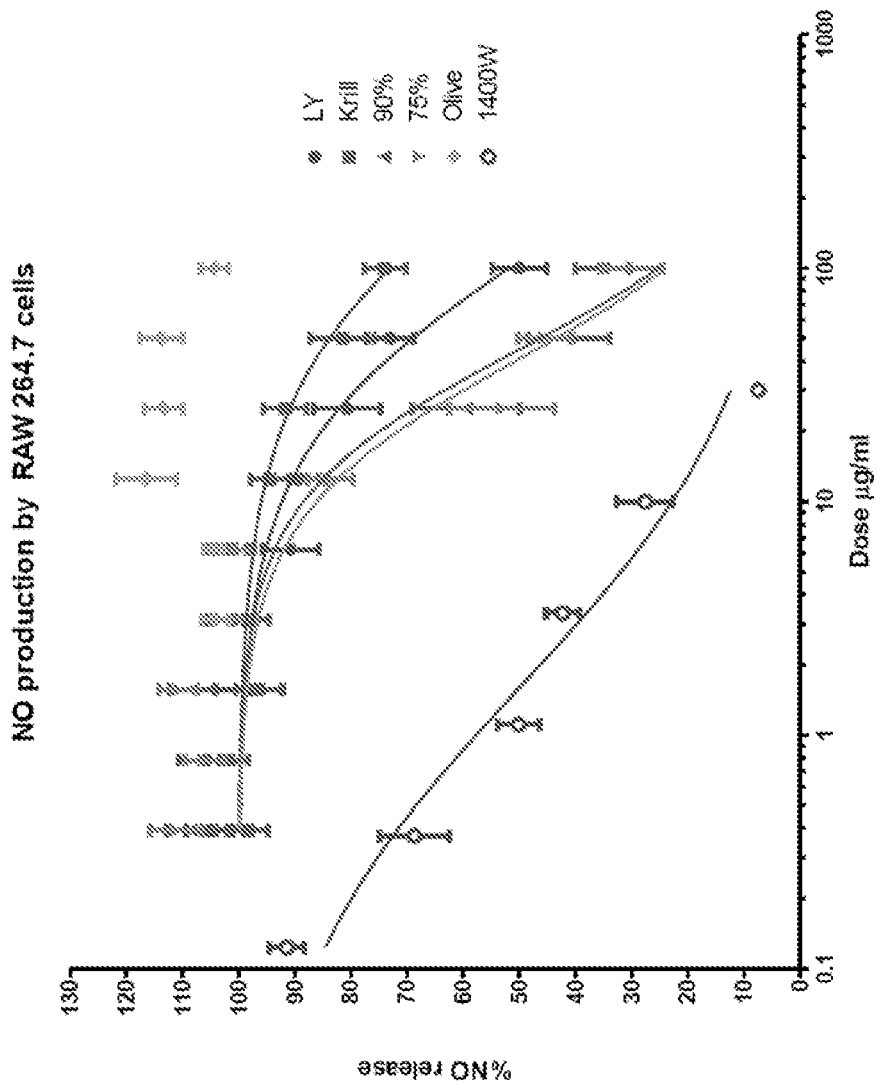

FIG. 1B graphically depicts NO release (%) in lipopolysaccharide (LPS) and interferon γ (IFγ) stimulated RAW264.7 cells for various concentrations of combinations of mussel lipid extract and krill oil, each of mussel lipid extract and krill oil alone, olive oil and N-(3-(Aminomethyl) benzyl)acetamidine (1400W).

Figure 2A:
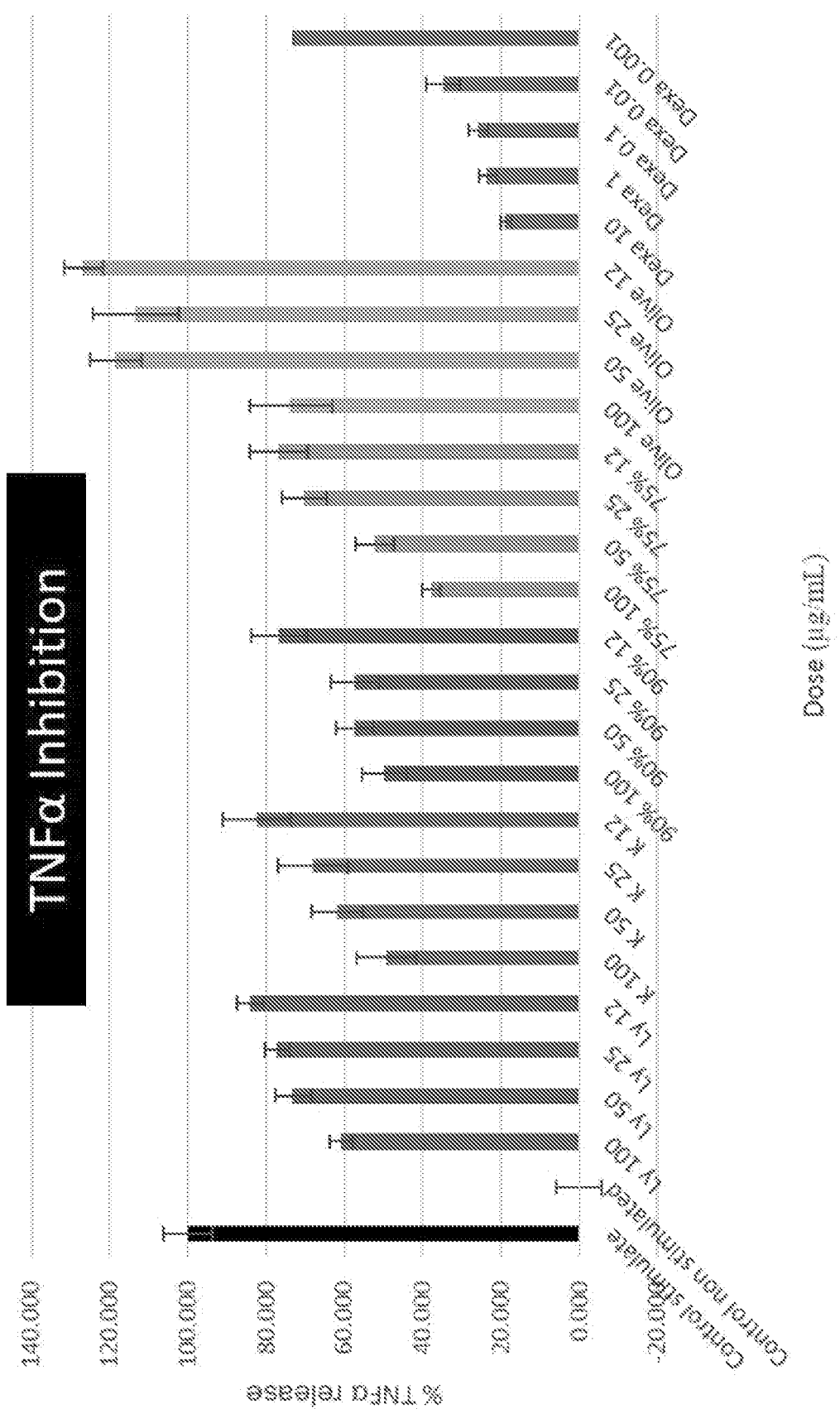

FIG. 2A graphically depicts the TNFα inhibition effect in lipopolysaccharide (LPS) and interferon γ (IFγ) stimulated RAW264.7 cells for various concentrations of combinations of mussel lipid extract and krill oil, each of mussel lipid extract and krill oil alone, olive oil and Dexamethasone.

Figure 2B:
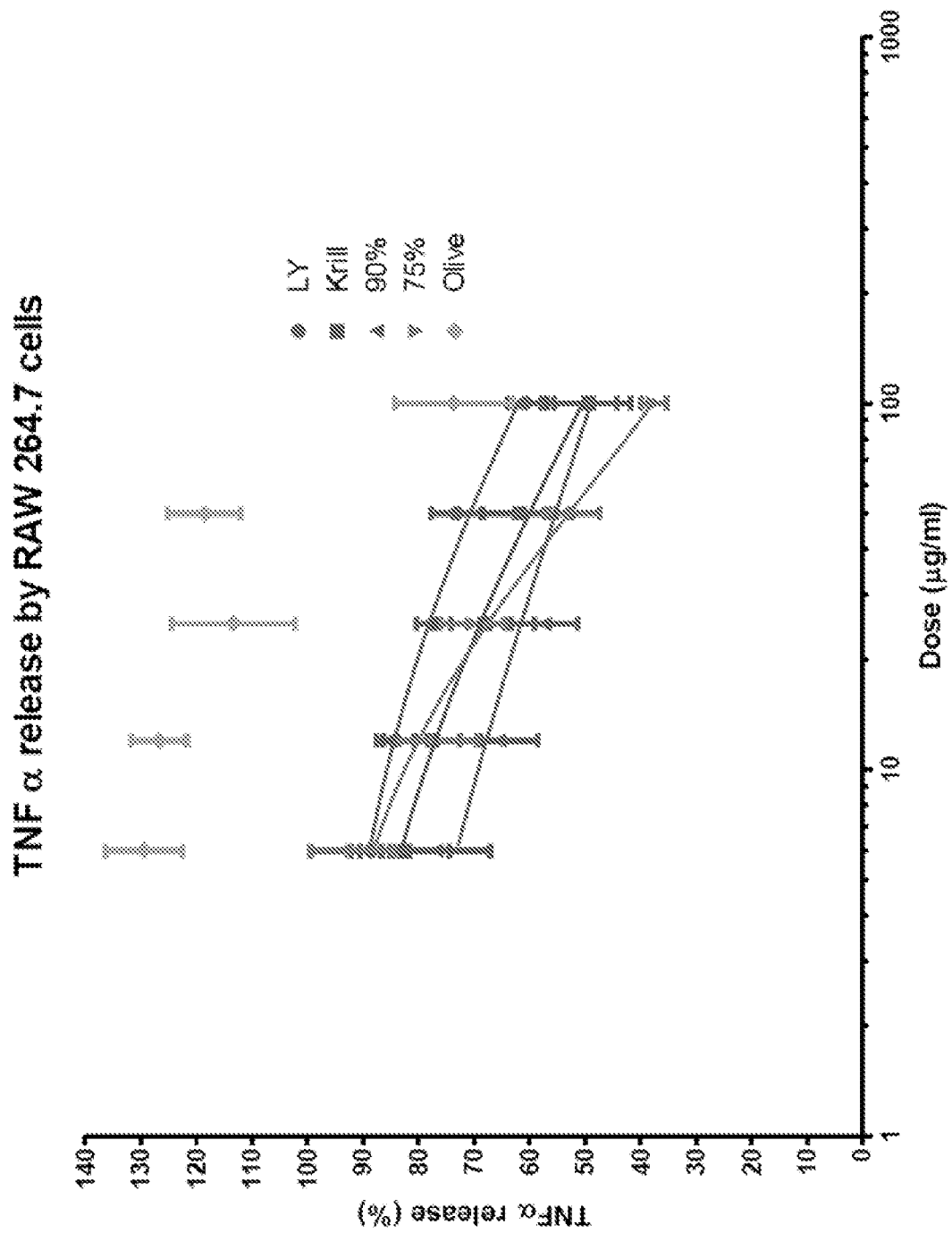

FIG. 2B graphically depicts TNFα release (%) in lipopolysaccharide (LPS) and interferon γ (IFγ) stimulated RAW264.7 cells for various concentrations of combinations of mussel lipid extract and krill oil, each of mussel lipid extract and krill oil alone and olive oil.

Figure 3A:
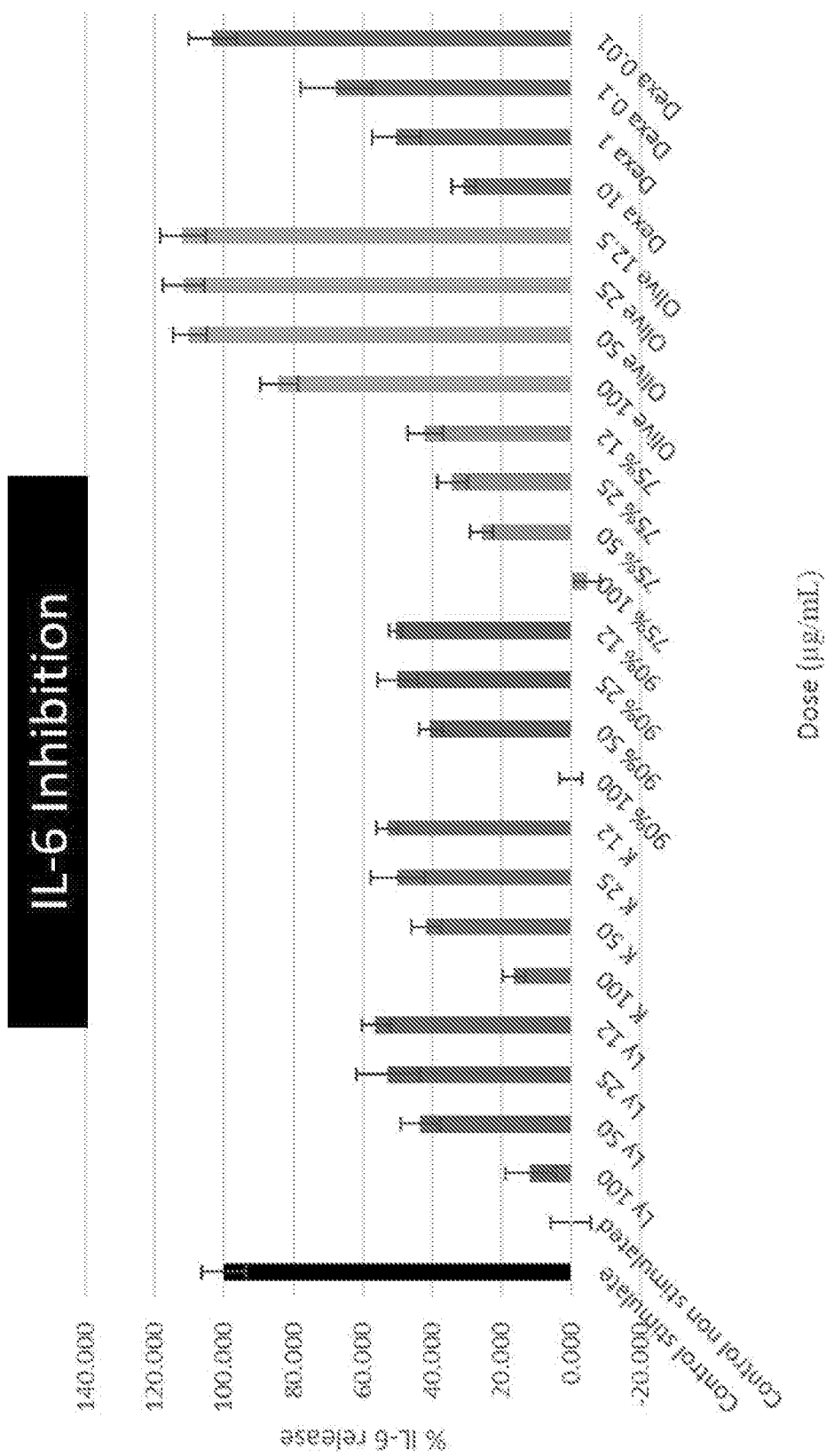

FIG. 3A graphically depicts the IL-6 inhibition effect in lipopolysaccharide (LPS) and interferon γ (IFγ) stimulated RAW264.7 cells for various concentrations of combinations of mussel lipid extract and krill oil, each of mussel lipid extract and krill oil alone, olive oil and Dexamethasone.

Figure 3B:
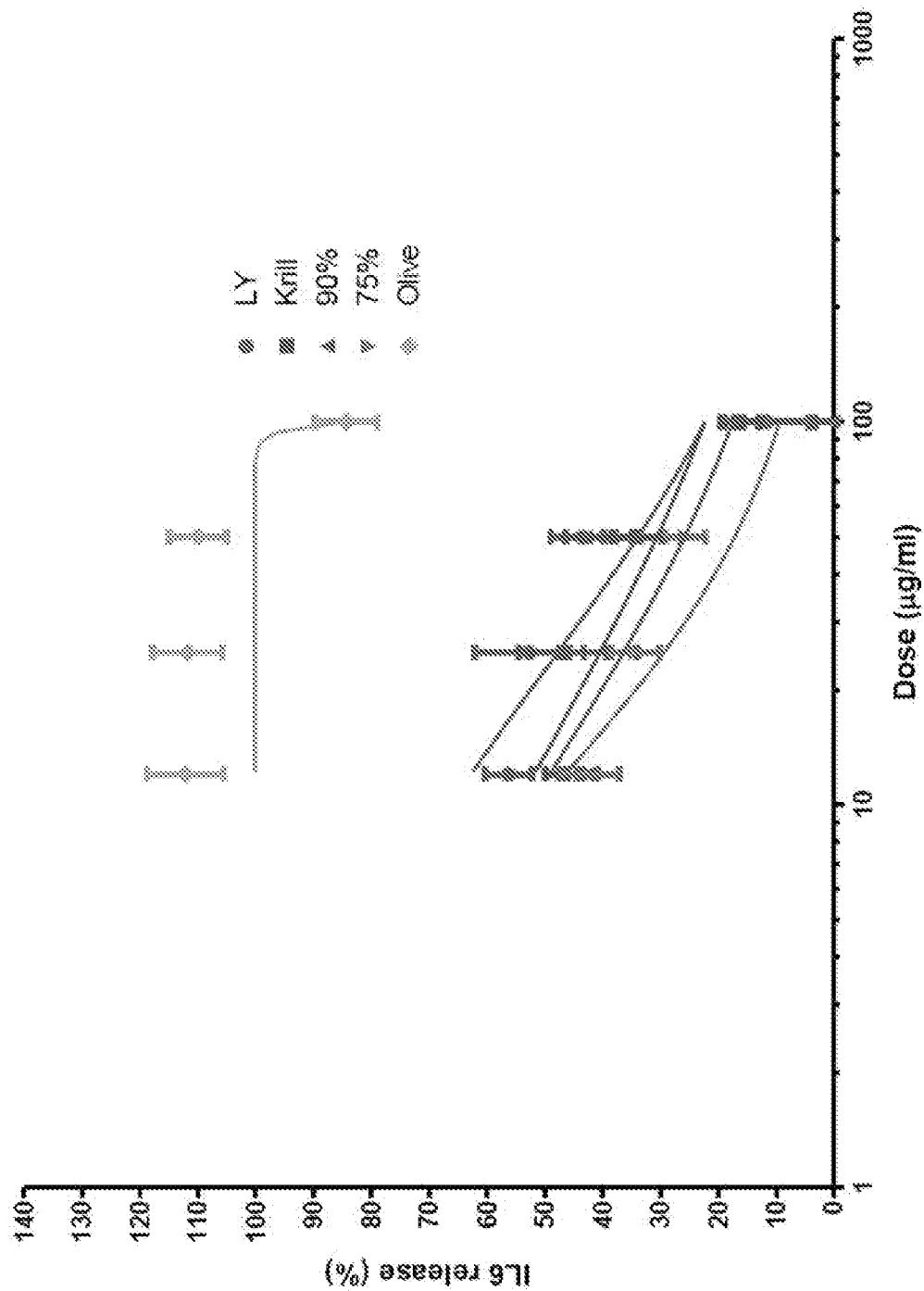

FIG. 3B graphically depicts the IL-6 release (%) in lipopolysaccharide (LPS) and interferon γ (IFγ) stimulated RAW264.7 cells for various concentrations of combinations of mussel lipid extract and krill oil, each of mussel lipid extract and krill oil alone, and olive oil.

Figure 4A:
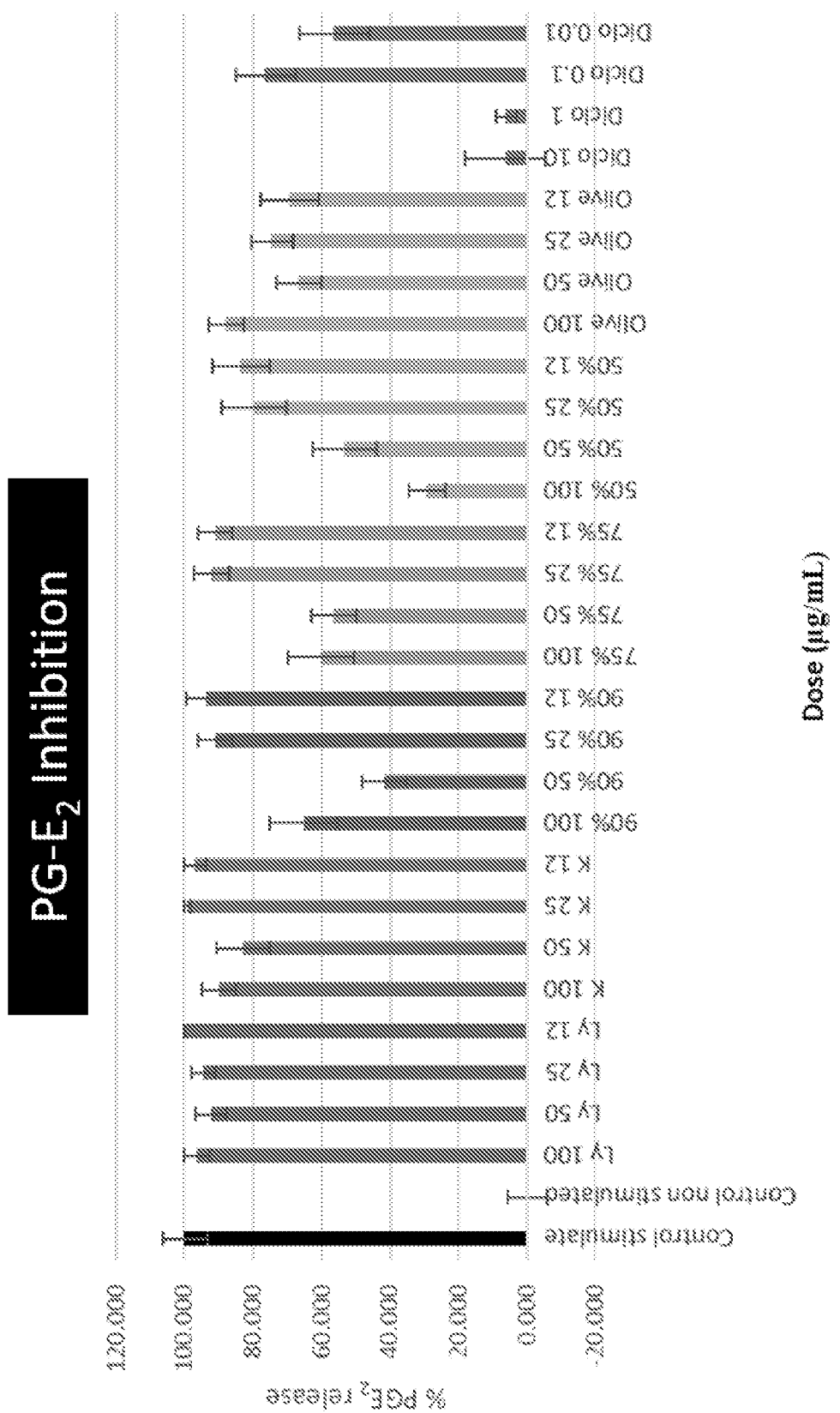

FIG. 4A graphically depicts the PGE2 inhibition effect in lipopolysaccharide (LPS) and interferon γ (IFγ) stimulated RAW264.7 cells for various concentrations of combinations of mussel lipid extract and krill oil, each of mussel lipid extract and krill oil alone, olive oil and diclofenac.

Figure 4B:
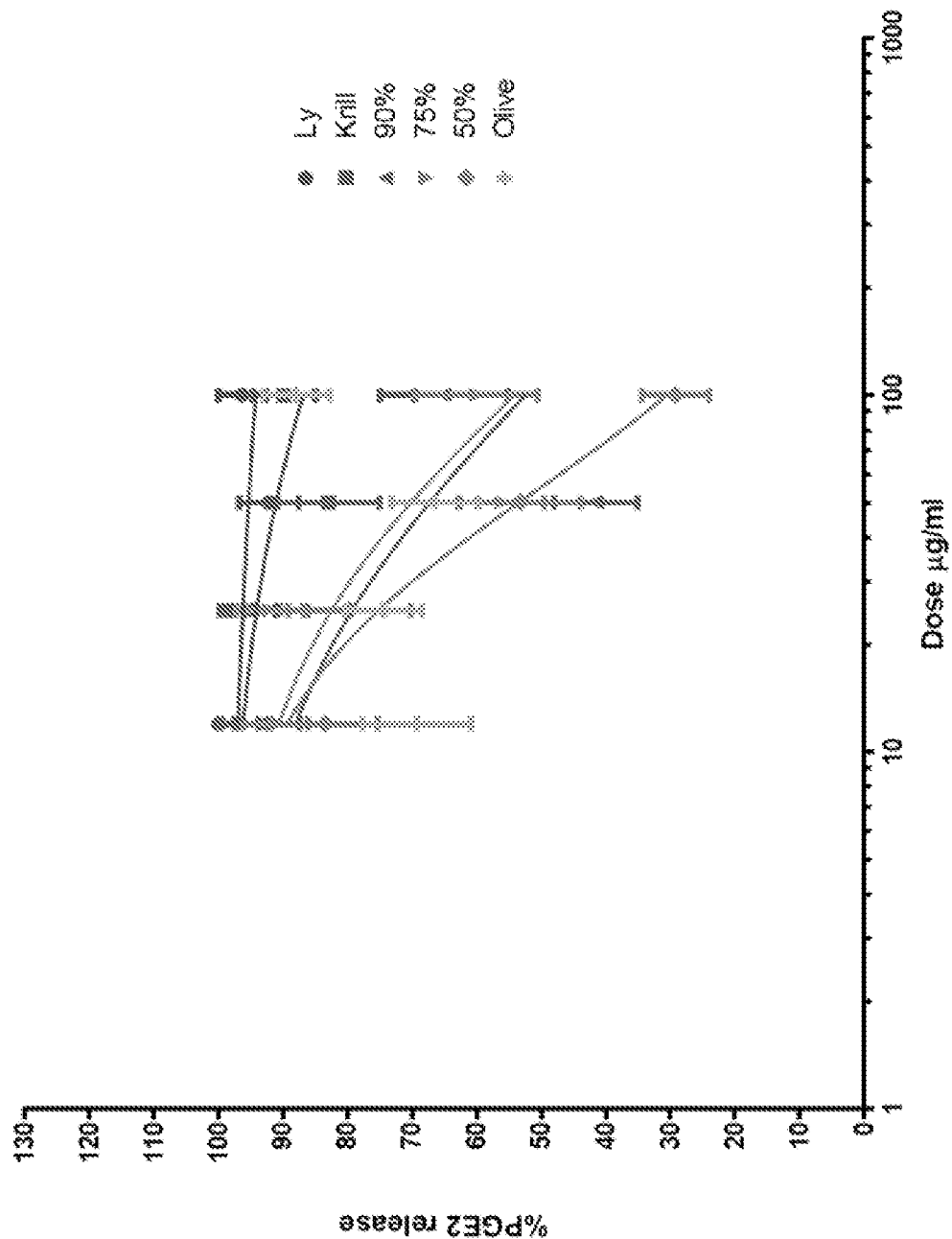

FIG. 4B graphically depicts the PGE2 release (%) in lipopolysaccharide (LPS) and interferon γ (IFγ) stimulated RAW264.7 cells for various concentrations of combinations of mussel lipid extract and krill oil, each of mussel lipid extract and krill oil alone, and olive oil.

Figure 5A:
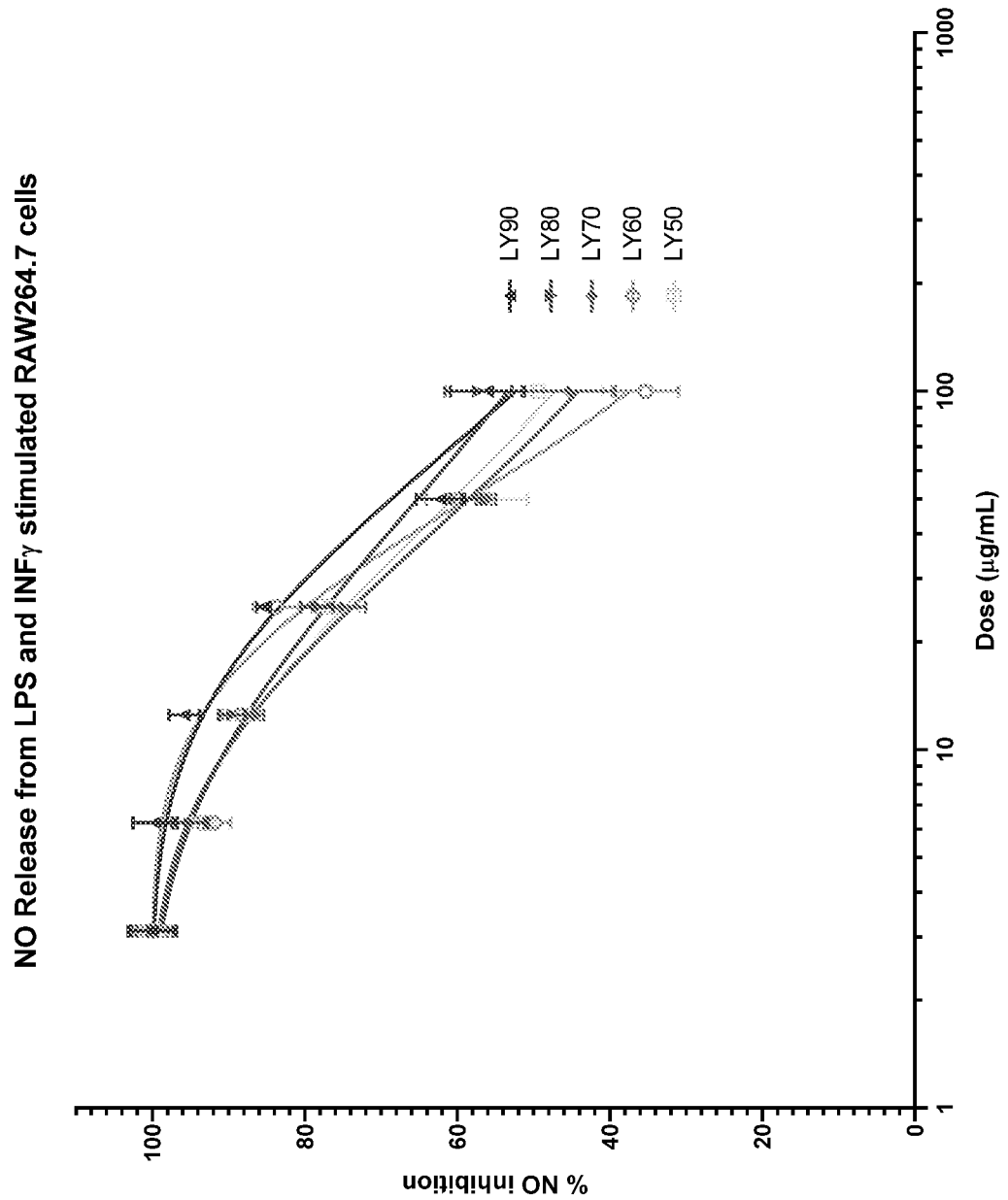

FIG. 5A graphically depicts NO release (%) in lipopolysaccharide (LPS) and interferon γ (IFγ) stimulated RAW264.7 cells for various concentrations of combinations of mussel lipid extract and krill oil (LY90-LY50).

Figure 5B:
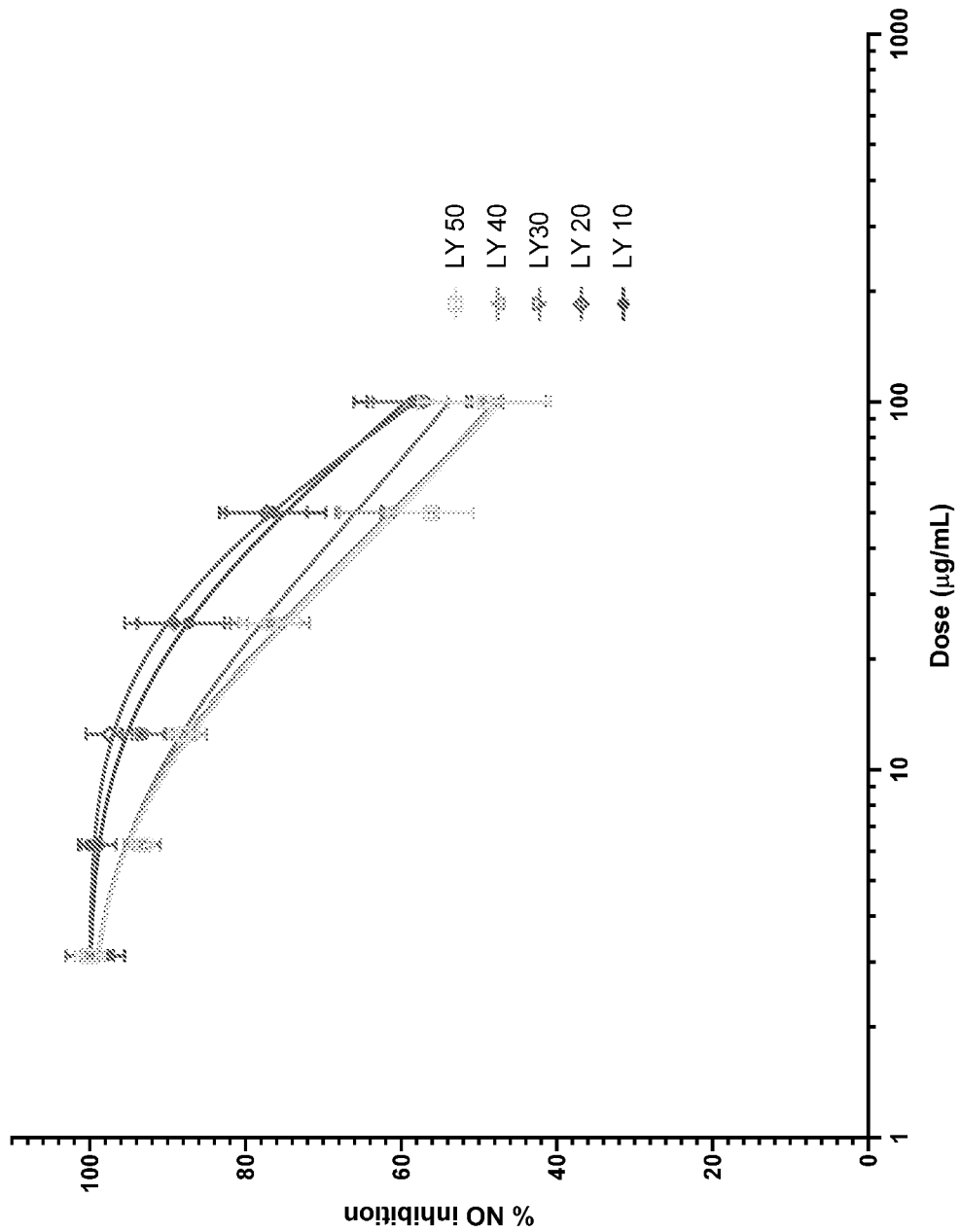

FIG. 5B graphically depicts NO release (%) in lipopolysaccharide (LPS) and interferon γ (IFγ) stimulated RAW264.7 cells for various concentrations of combinations of mussel lipid extract and krill oil (LY50-LY10).

Figure 6A:
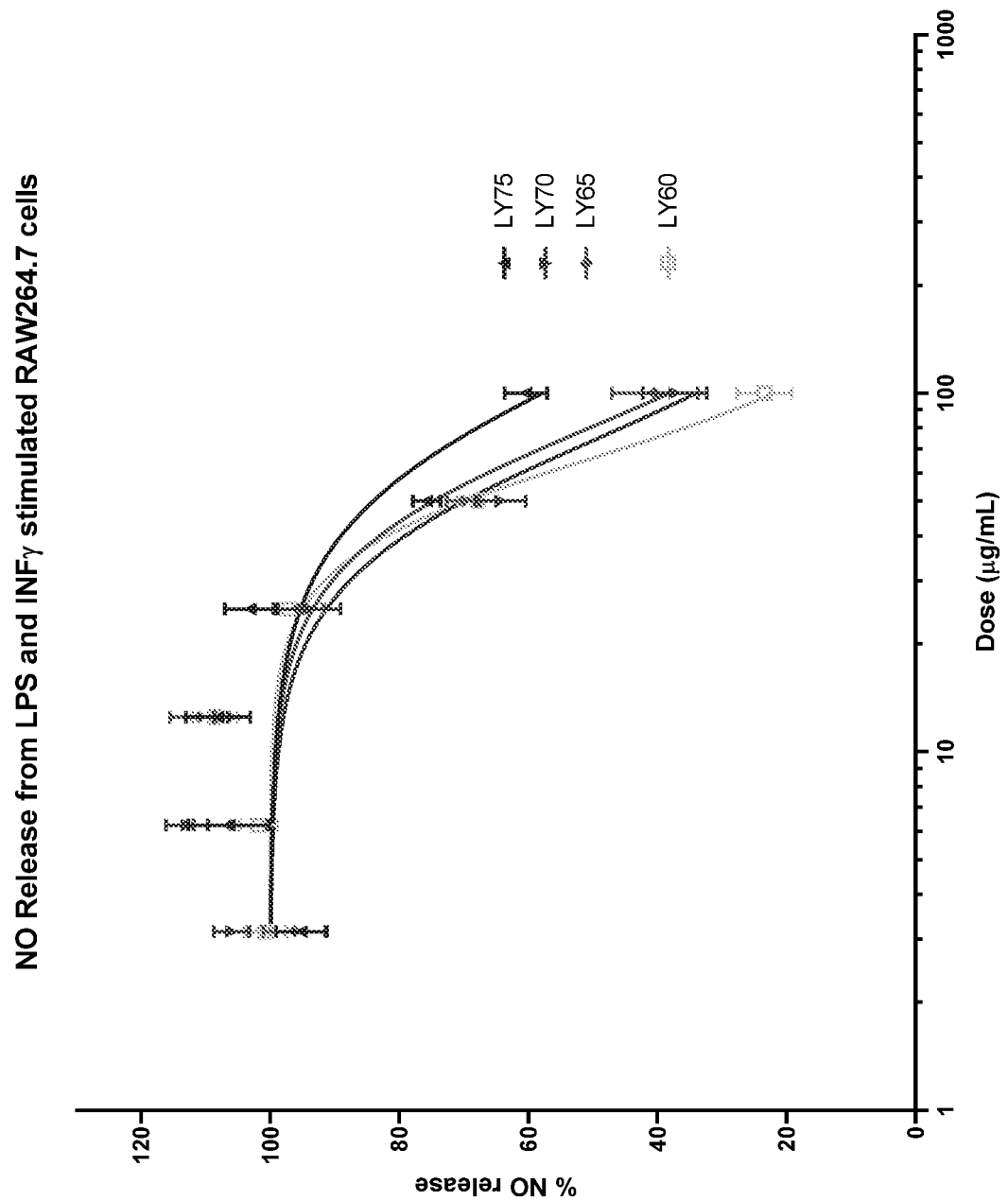

FIG. 6A graphically depicts NO release (%) in lipopolysaccharide (LPS) and interferon γ (IFγ) stimulated RAW264.7 cells for various concentrations of combinations of mussel lipid extract and krill oil (LY75-LY60).

Figure 6B:
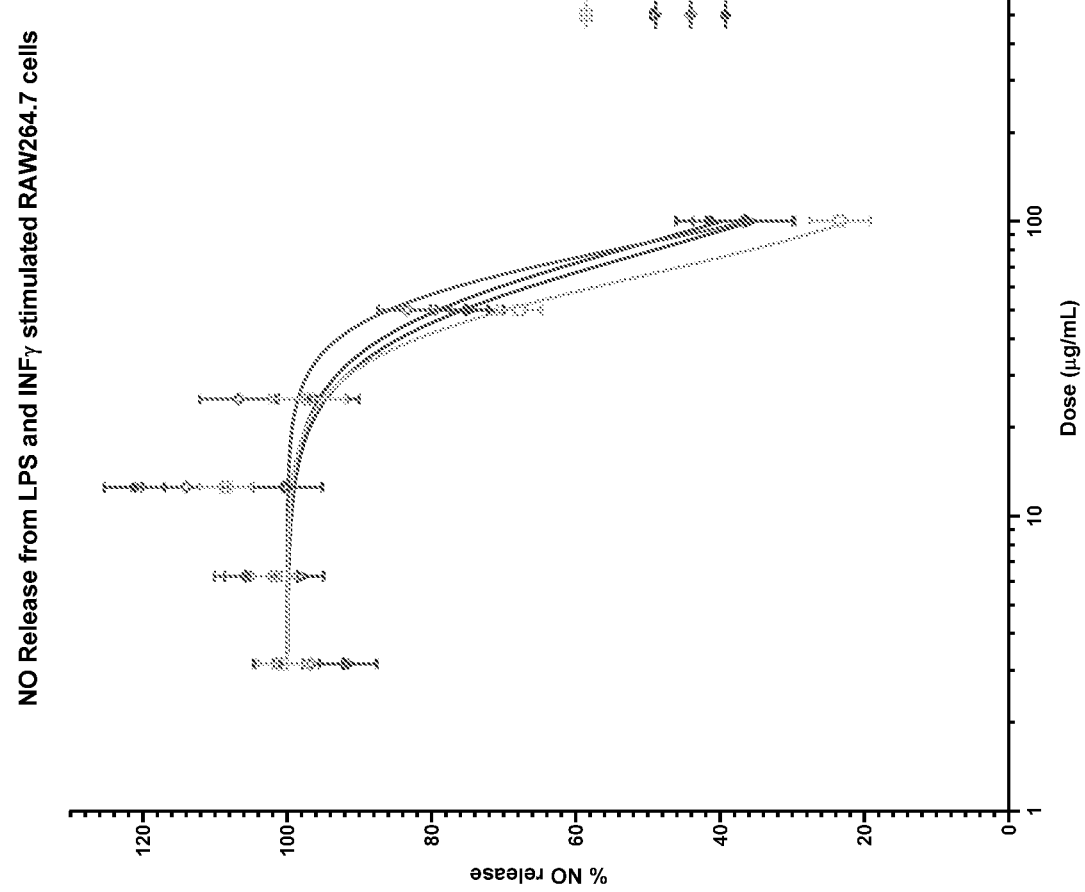

FIG. 6B graphically depicts NO release (%) in lipopolysaccharide (LPS) and interferon γ (IFγ) stimulated RAW264.7 cells for various concentrations of combinations of mussel lipid extract and krill oil (LY60-LY45).

Figure 7:
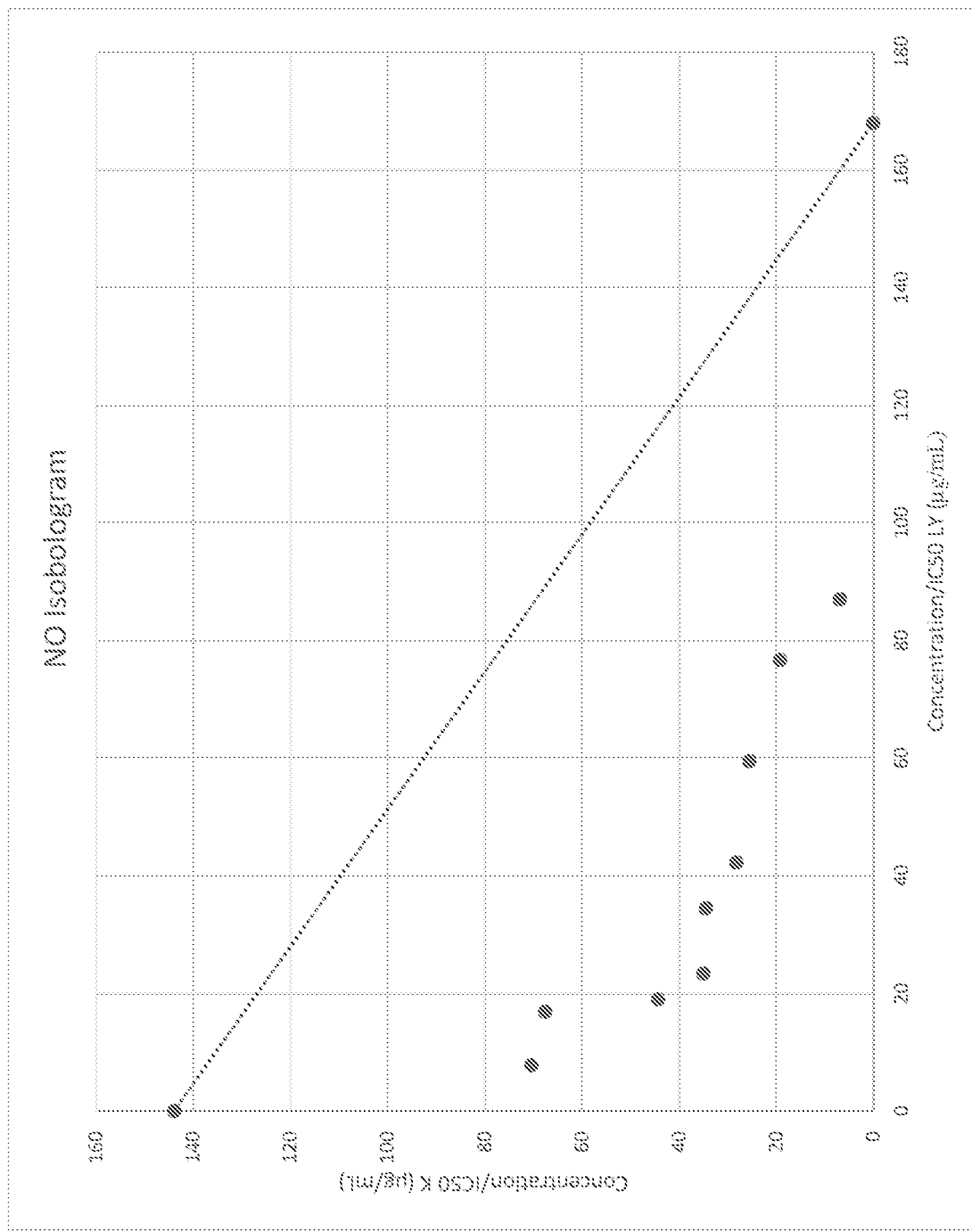

FIG. 7 graphically depicts the isobologram for synergistic NO inhibition by various concentrations of combinations of mussel lipid extract and krill oil (LY90-LY10).

Figure 8A:
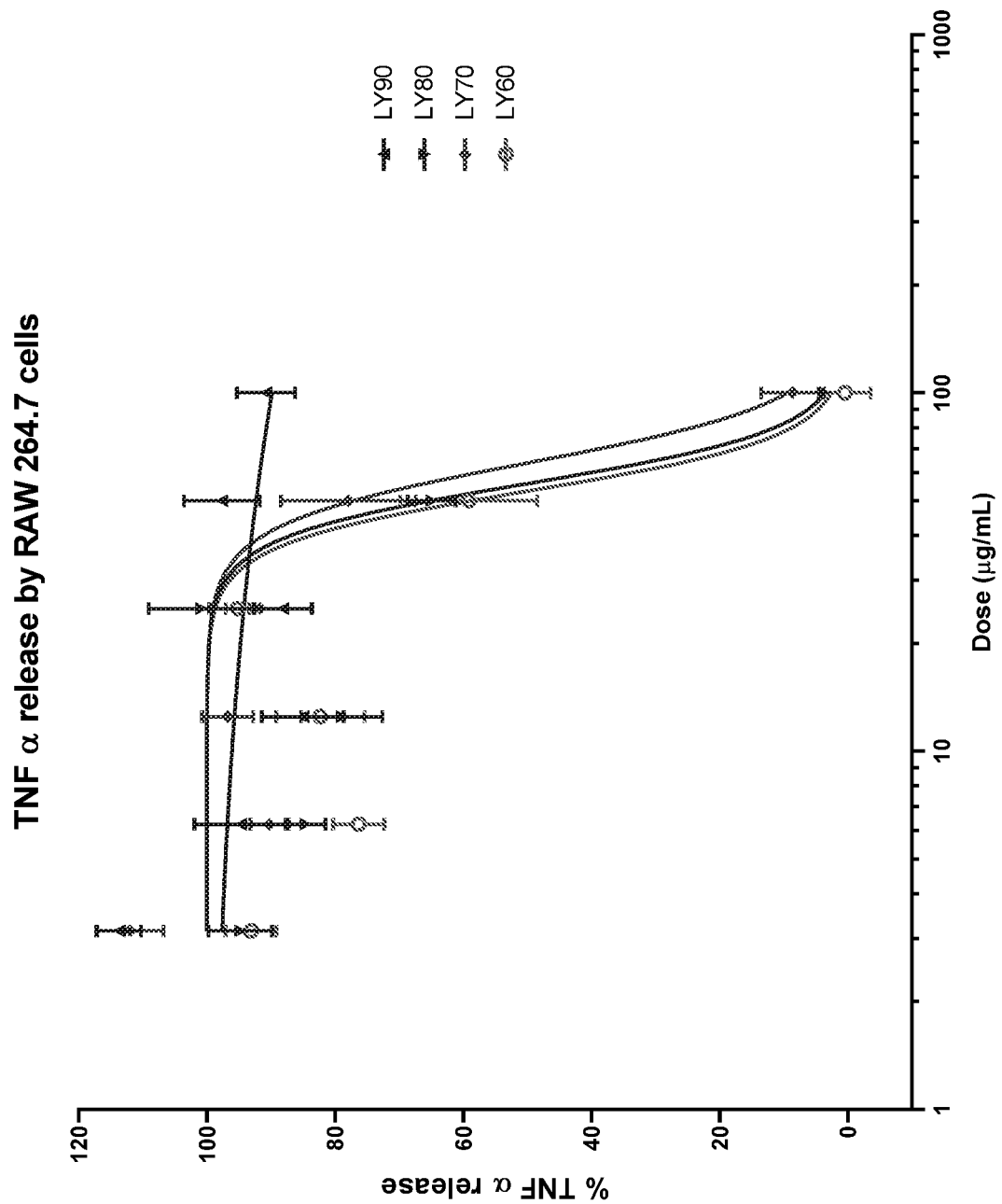

FIG. 8A graphically depicts TNFα release (%) in lipopolysaccharide (LPS) and interferon γ (IFγ) stimulated RAW264.7 cells for various concentrations of combinations of mussel lipid extract and krill oil (LY90-LY60).

Figure 8B:
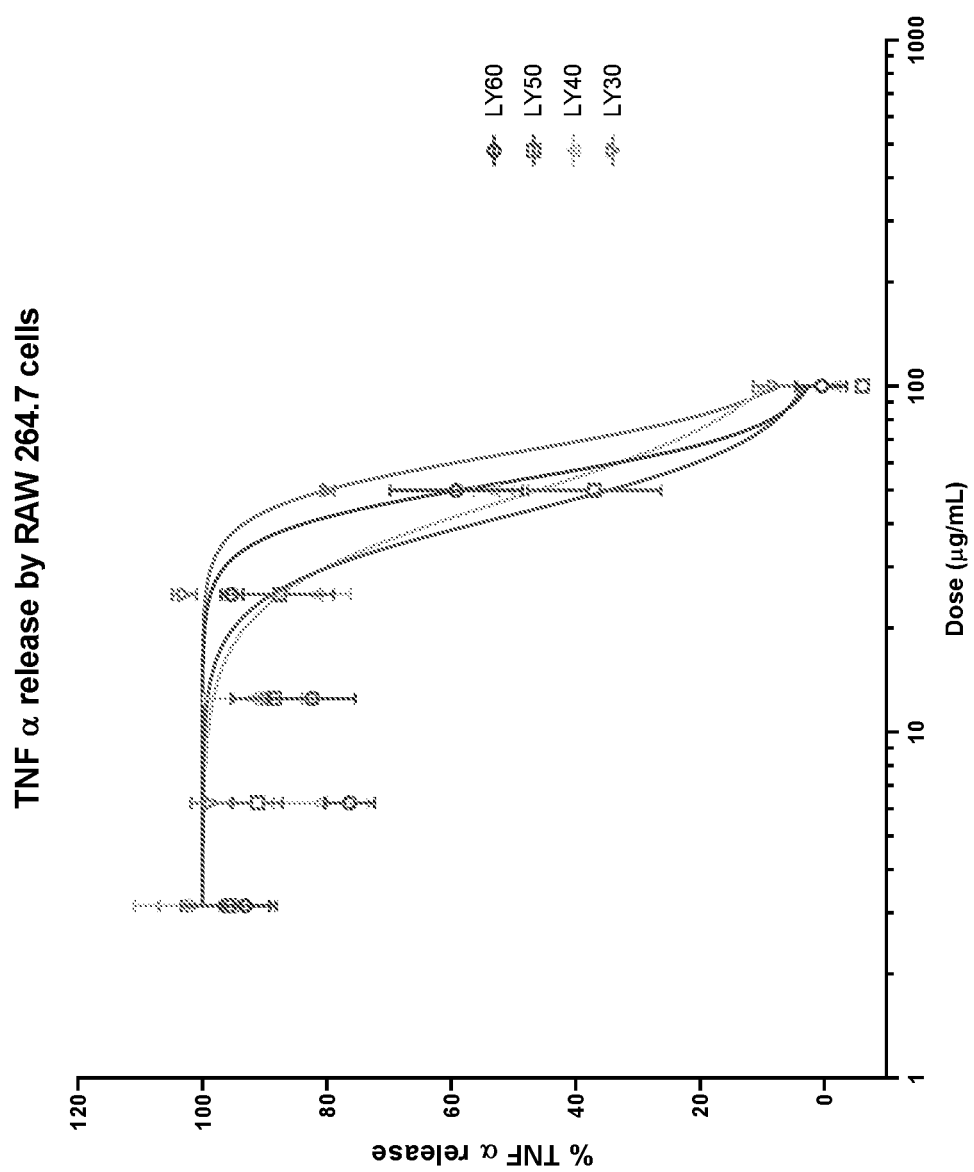

FIG. 8B graphically depicts TNFα release (%) in lipopolysaccharide (LPS) and interferon γ (IFγ) stimulated RAW264.7 cells for various concentrations of combinations of mussel lipid extract and krill oil (LY60-LY30).

Figure 8C:
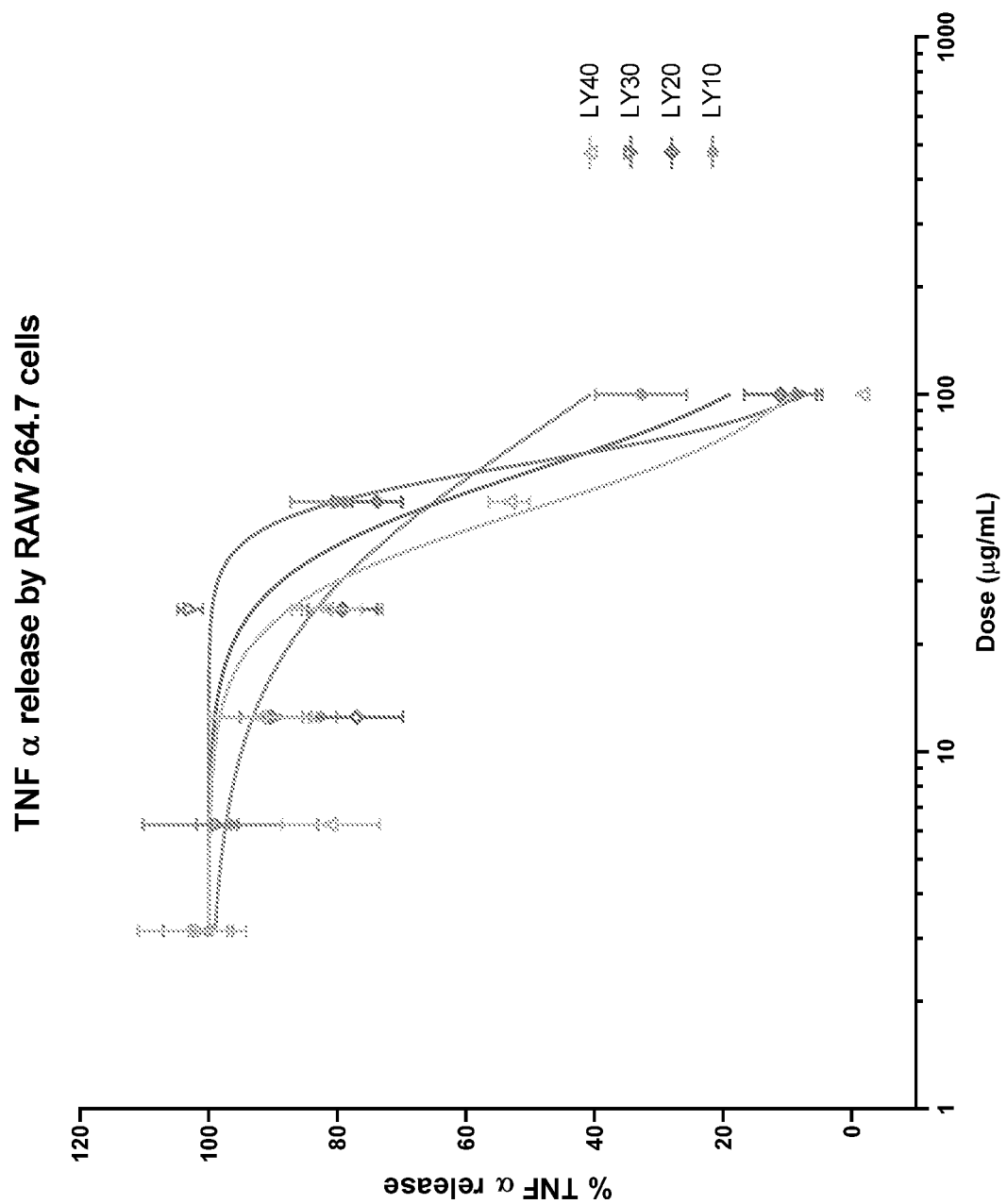

FIG. 8C graphically depicts TNFα release (%) in lipopolysaccharide (LPS) and interferon γ (IFγ) stimulated RAW264.7 cells for various concentrations of combinations of mussel lipid extract and krill oil (LY40-LY10).

Figure 9A:
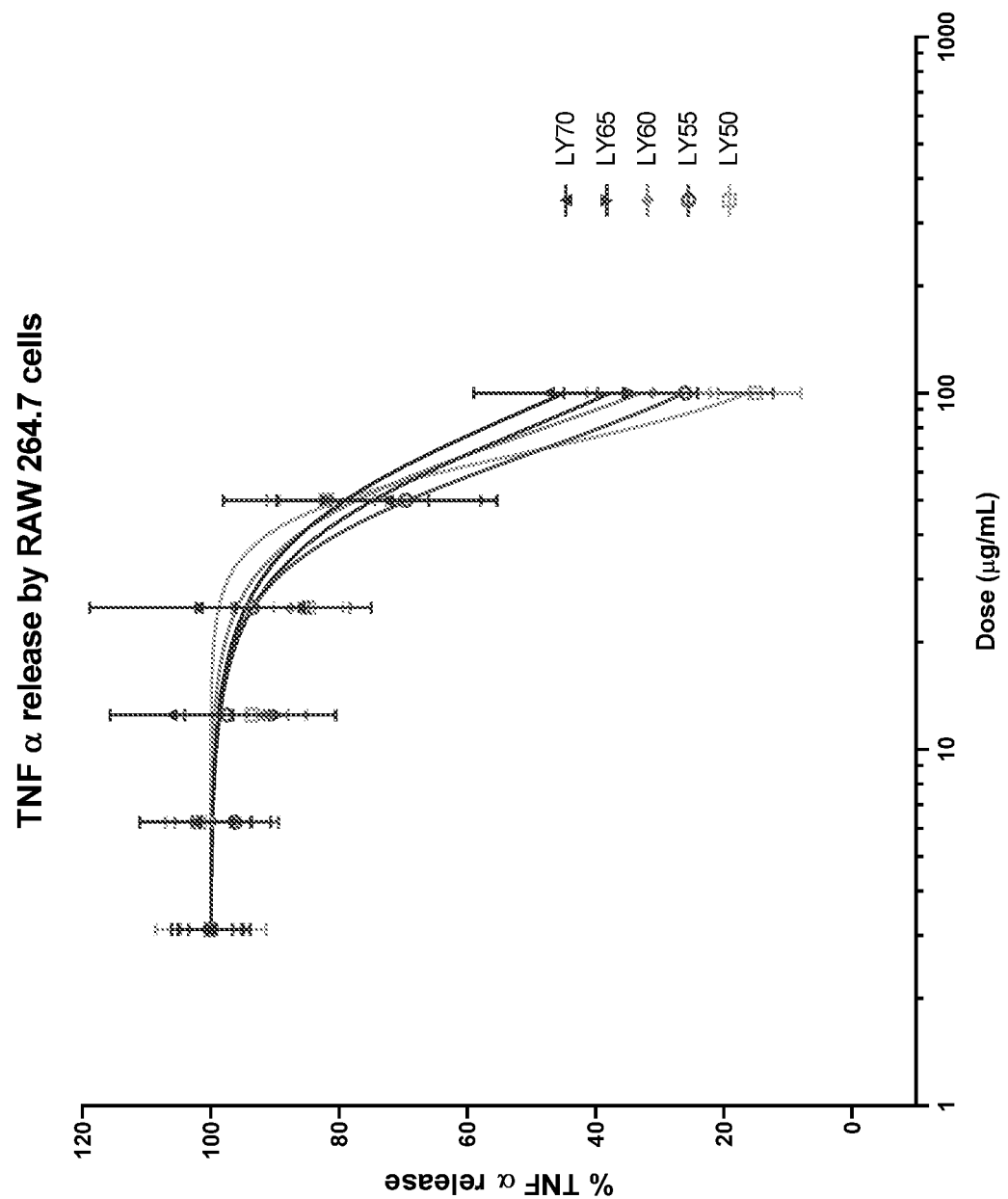

FIG. 9A graphically depicts TNFα release (%) in lipopolysaccharide (LPS) and interferon γ (IFγ) stimulated RAW264.7 cells for various concentrations of combinations of mussel lipid extract and krill oil (LY70-LY55).

Figure 9B:
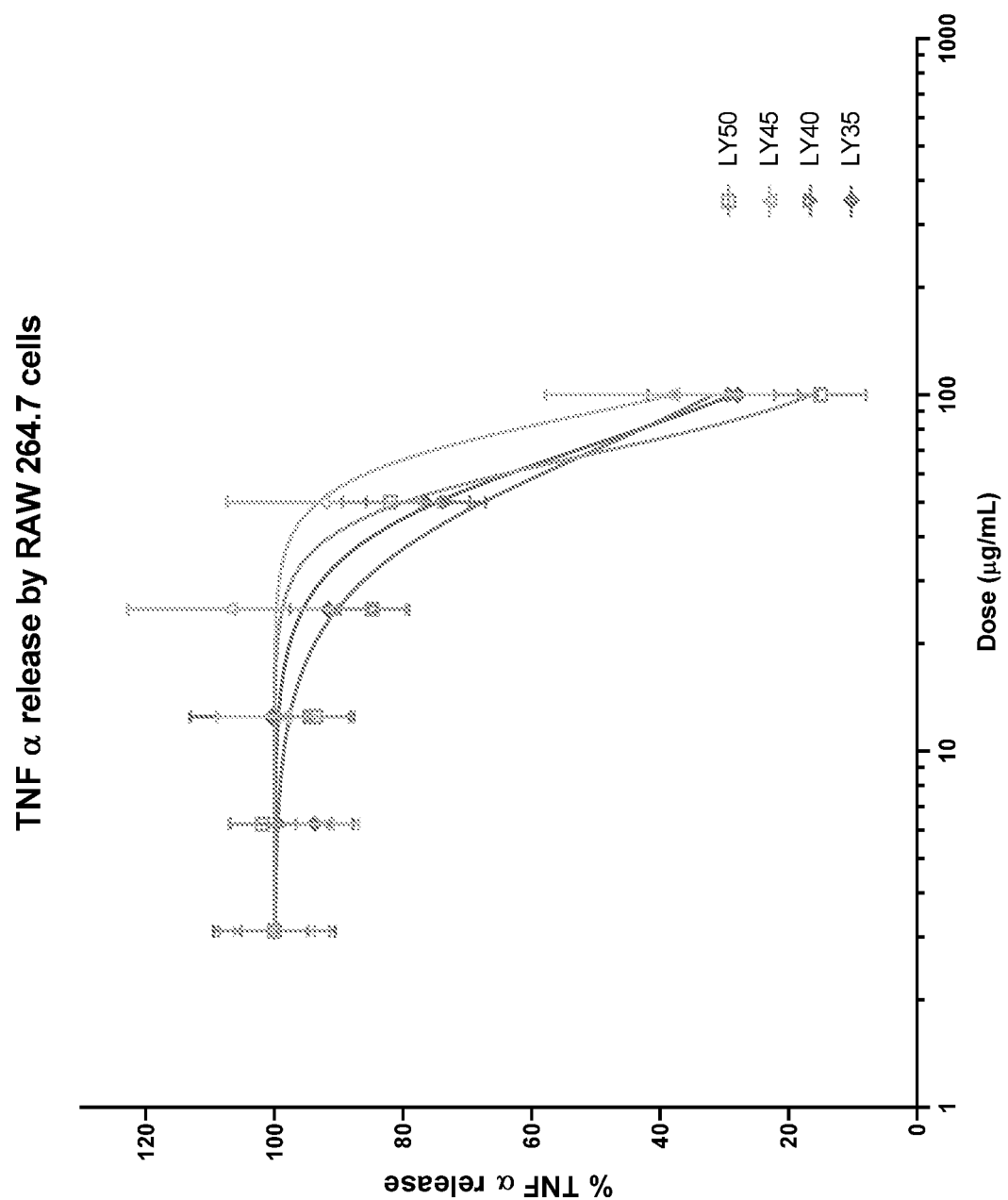

FIG. 9B graphically depicts TNFα release (%) in lipopolysaccharide (LPS) and interferon γ (IFγ) stimulated RAW264.7 cells for various concentrations of combinations of mussel lipid extract and krill oil (LY50-LY35).

Figure 10:
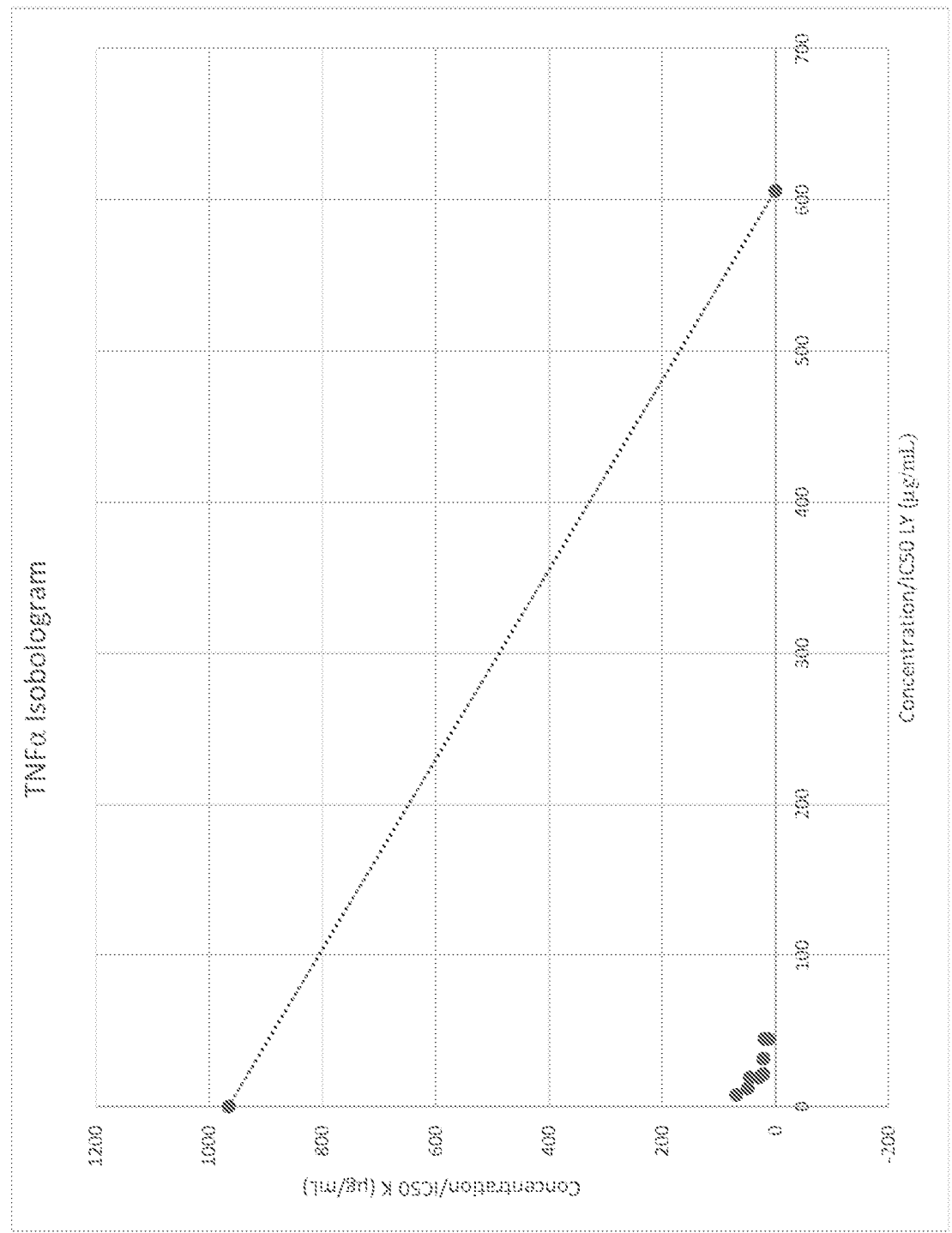

FIG. 10 graphically depicts the isobologram for synergistic TNFα inhibition by various concentrations of combinations of mussel lipid extract and krill oil (LY90-LY10).

Figure 11A:
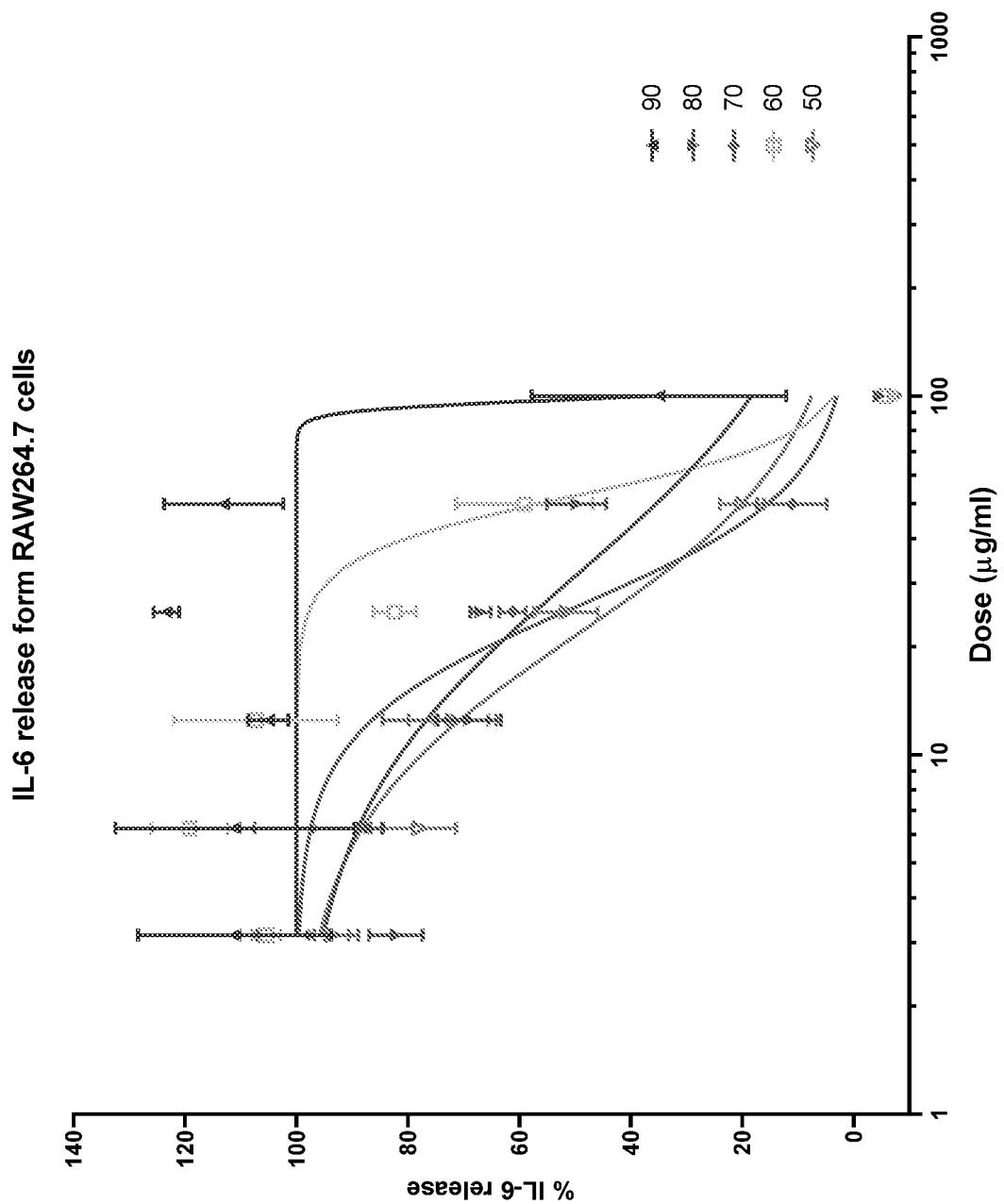

FIG. 11A graphically depicts the IL-6 release (%) in lipopolysaccharide (LPS) and interferon γ (IFγ) stimulated RAW264.7 cells for various concentrations of combinations of mussel lipid extract and krill oil (LY90-LY50).

Figure 11B:
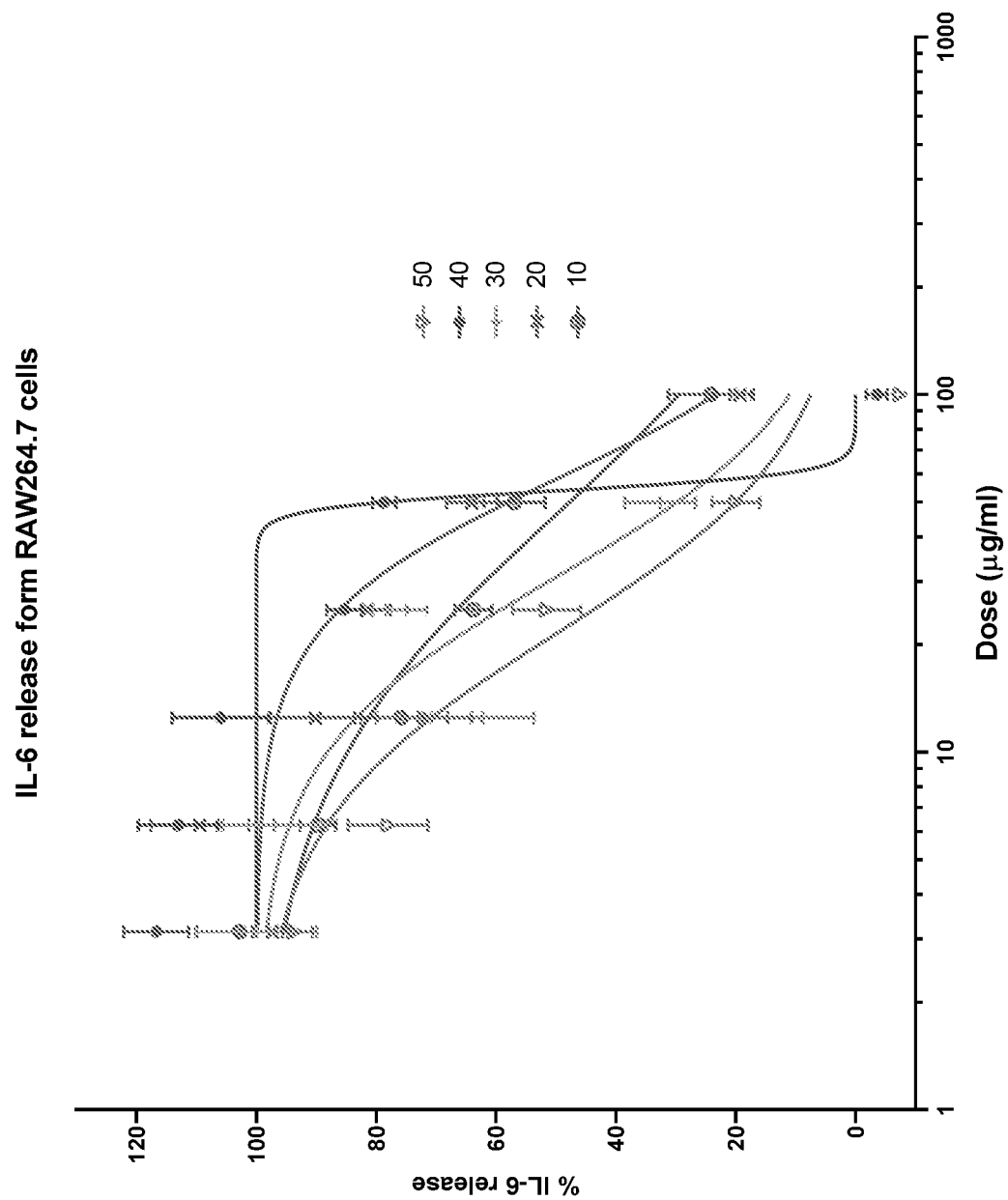

FIG. 11B graphically depicts the IL-6 release (%) in lipopolysaccharide (LPS) and interferon γ (IFγ) stimulated RAW264.7 cells for various concentrations of combinations of mussel lipid extract and krill oil (LY50-LY10).

Figure 12A:
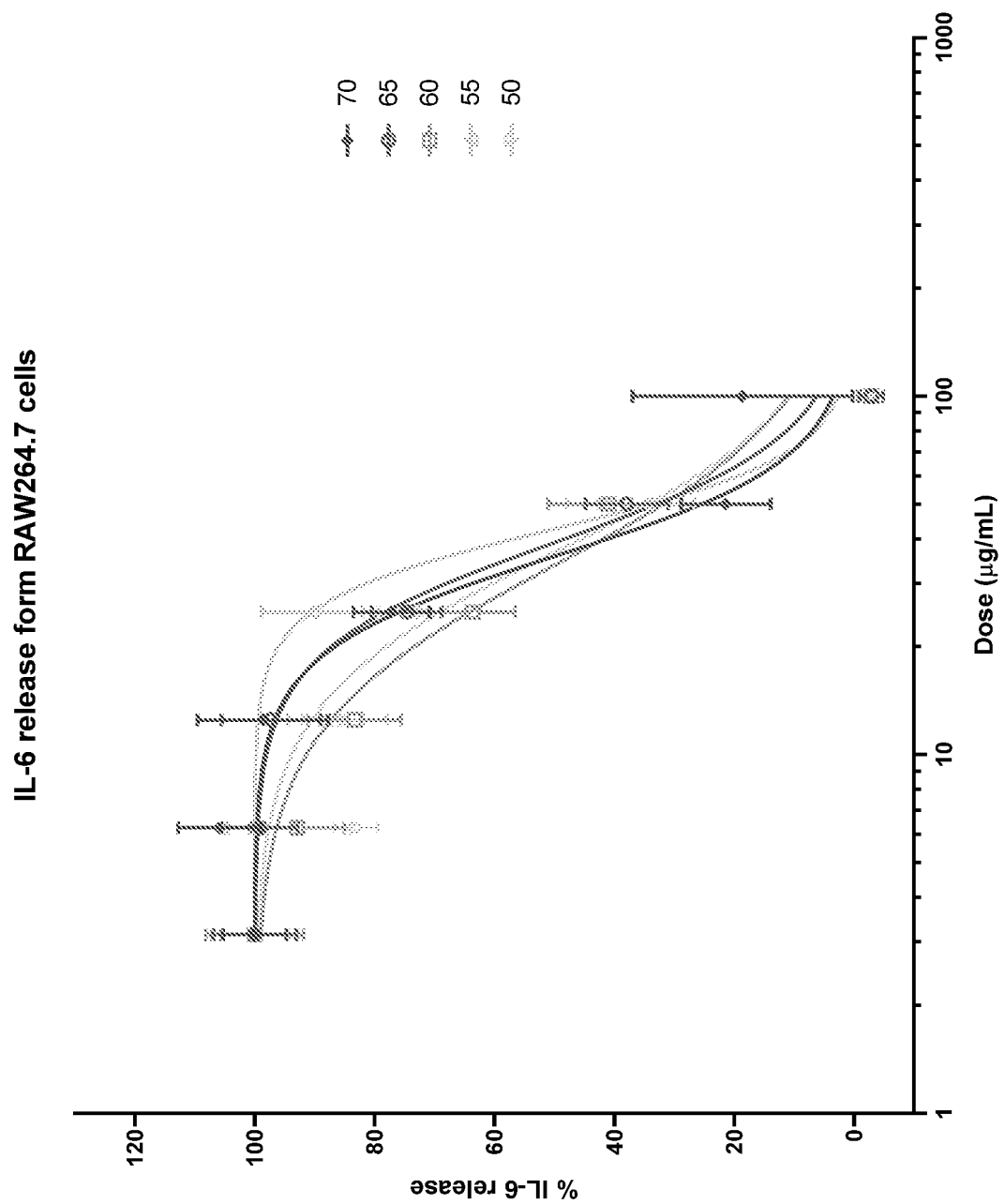

FIG. 12A graphically depicts the IL-6 release (%) in lipopolysaccharide (LPS) and interferon γ (IFγ) stimulated RAW264.7 cells for various concentrations of combinations of mussel lipid extract and krill oil (LY70-LY50).

Figure 12B:
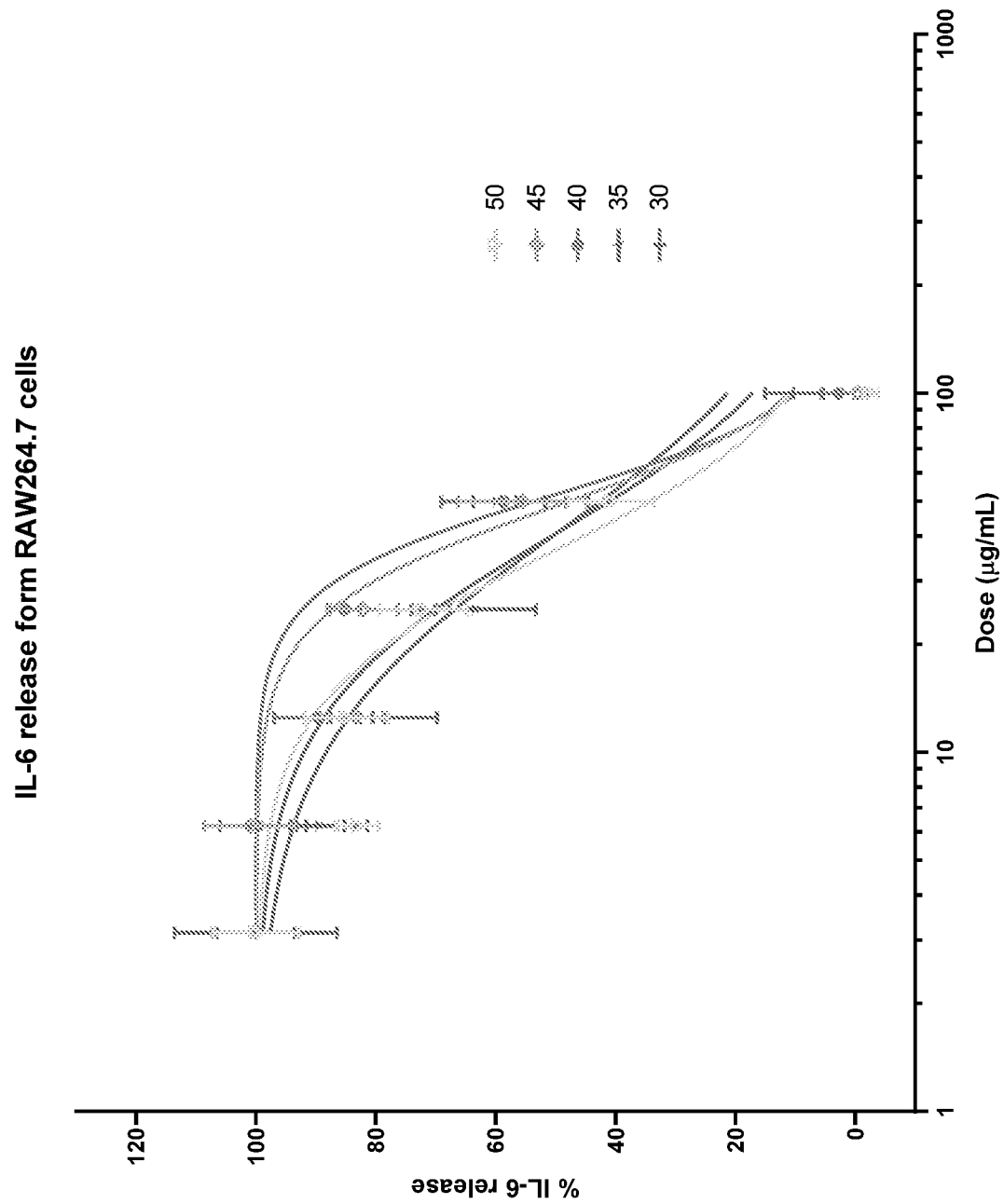

FIG. 12B graphically depicts the IL-6 release (%) in lipopolysaccharide (LPS) and interferon γ (IFγ) stimulated RAW264.7 cells for various concentrations of combinations of mussel lipid extract and krill oil (LY50-LY30).

Figure 13:
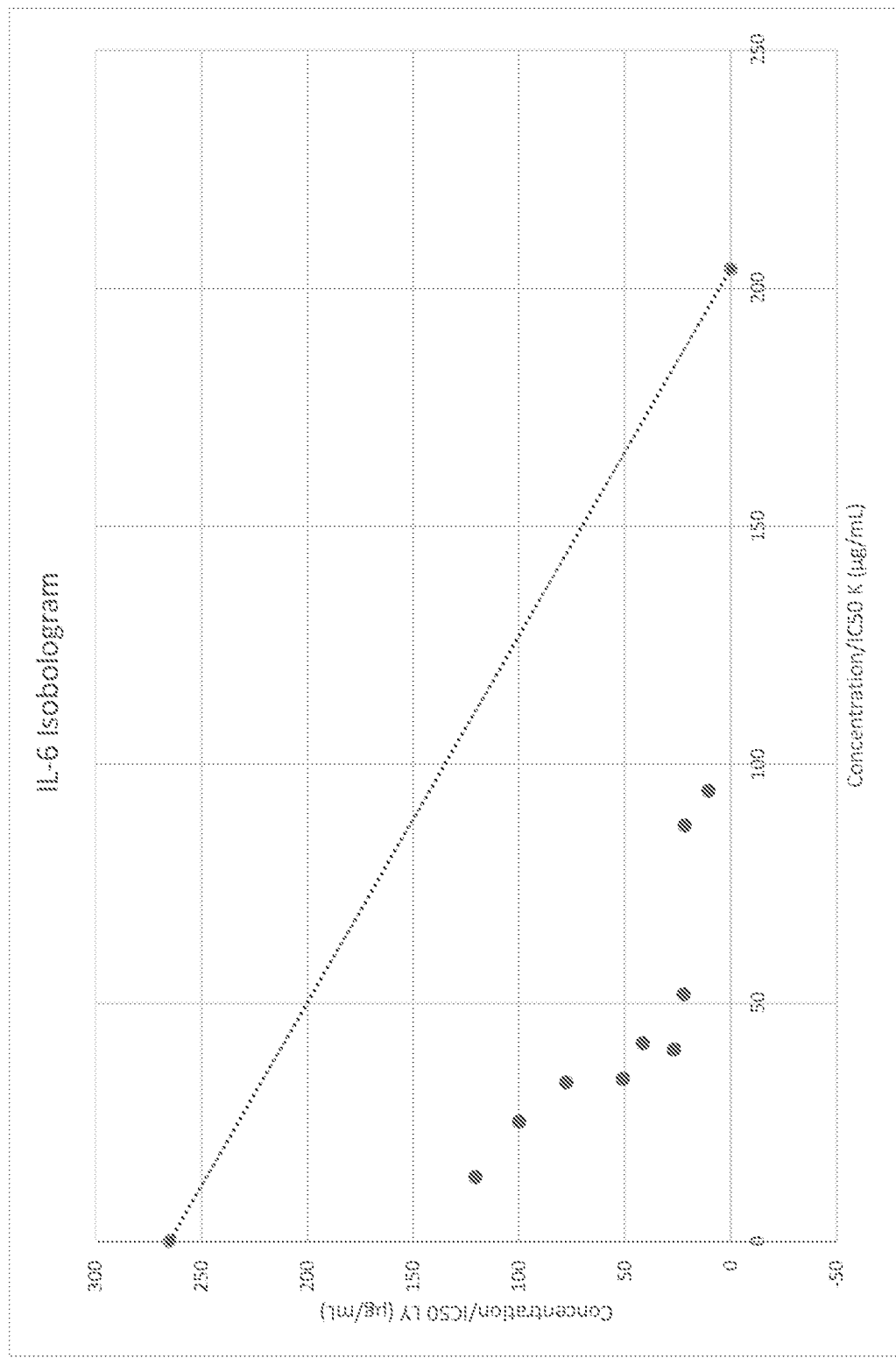

FIG. 13 graphically depicts the isobologram for synergistic IL-6 inhibition by various concentrations of combinations of mussel lipid extract and krill oil (LY90-LY10).

DESCRIPTION

Throughout this specification and the claims which follow, unless the context requires otherwise, the word "comprise" and variations such as "comprises" and "comprising" will be understood to imply the inclusion of a stated integer or step or group of integers but not the exclusion of any other integer or step or group of integers or steps.

Throughout this specification and the claims which follow, unless the context requires otherwise the phrase "consisting essentially of" and variations such as "consists essentially of" will be understood to indicate that the recited element(s) is/are essential i.e. necessary elements of the invention. The phrase allows for the presence of other non-recited elements which do not materially affect the characteristics of the invention but excludes additional unspecified elements which would affect the basic and novel characteristics of the invention defined.

The singular forms "a", "an" and "the" include plural aspects unless the context clearly dictates otherwise.

The term "invention" includes all disclosures, aspects, embodiments and examples as described herein.

As used herein, "about" refers to a quantity, value or parameter that may vary by as much as 10%, 5%, or 2-1% of the stated quantity, value or parameter, and includes at least tolerances accepted within the art. When used in reference to a stated whole number value, "about" may include variation of one whole number either side of the stated value, for example "50%", may include 49% and 51%. When prefacing a recited range of values, it is intended to apply to both upper and lower limits of the range.

Unless the context indicates otherwise, features described below may apply independently to any aspect or embodiment.

As used herein, "mussel lipid" refers to a lipid component extracted or obtained from the New Zealand green-lipped (NZGL) (or greenshell) mussel (*Perna canaliculus*). The mussel lipid may comprise one or more of polyunsaturated long chain fatty acids (PUFAs), such as ALA, ETAs, EPA and DHA, sterols, sterol esters, triglycerides, non-polar lipds carotenoids and other components of (NZGL) mussel meat. The mussel lipid may be in the form of dried mussel powder, or a lipid fraction extracted from the mussel meat ("mussel lipid extract"). It is also envisaged that "mussel lipid" encompasses a mixture of a mussel powder and mussel lipid extract, for example a mussel lipid may be supplemented by the addition of mussel powder or vice versa. In some embodiments, the mussel lipid is an isolated lipid fraction.

The mussel lipid powder may be prepared from fresh (raw), frozen or heat treated NZGL mussel meat by any suitable drying means (e.g. freeze drying, flash drying or vacuum drying) and pulverizing means. In addition to fatty acids (including ALA, ETAs, EPA and DHA) the mussel powder obtained by drying mussel meat will also contain other potentially beneficial components, including minerals, amino acids, peptides, proteins, and glycosaminoglycans (for example chondroitin-4-sulfate and chondroitin-6-sulfate). Processes for preparing mussel powder are known in the art.

The mussel lipid extract may be obtained from fresh (raw), frozen, heat treated or dried (e.g. freeze-, flash- or vacuum drum-dried) NZGL mussel meat (e.g. powdered, spray dried or pulverized form) by any suitable method, such as solvent extraction (e.g. acetone or ethanol see for example WO2005073354 A1, the contents of which are incorporated by reference), enzyme treatment (see for example WO2006128244, the contents of which are incorporated by reference) or supercritical fluid extraction. In some embodiments, the mussel lipid extract is advantageously obtained by extraction with supercritical $CO_2$ from dried (e.g. freeze-dried) mussel meat (optionally stabilized to prevent oxidation). An exemplary method for obtaining mussel lipid extract is described in WO 97/09992 A1, the contents of which are incorporated by reference. Other methods will be known in the art.

In preferred embodiments processes are performed under conditions such that the beneficial components, such as fatty acids, not substantially destroyed and are significantly retained, for example cold processing.

One exemplary mussel lipid extract obtained in accordance with the process described in WO 97/09992 A1, is also known as PCSO-524® (Pharmalink International Limited, Hong Kong). PCSO-524® contains added vitamin E (0.15% w/w, added as an anti-oxidant preservative) and comprises a combination of free fatty acids, triglycerides, sterol esters, non-polar lipids, and carotenoids (Sinclair, A. J. et al, 2000), and is a source of the long chain omega-3 polyunsaturated fatty acids, eicosapentaenoic acid (EPA) and docosahexaenoic acid (DHA), as well as other long chain fatty acids, such as 5,9,12,15-octadecatetraenoic acid, 5,9,12,16-nonadecatetraenoic acid, 7,11,14,17-eicotetraenoic acid, and 5,9,12,15,18-heneicosapentaenoic acid. PCSO-254® (formulated together with olive oil in encapsulated oral dosage form), is marketed under the banner Lyprinol® and Omega XL®, (for human consumption), and Antinol® (for dogs and cats).

In some embodiments, the mussel lipid extract used in the combinations of the disclosure is formulated with vitamin E, (added, for example in an amount of about 0.2% w/w, or 0.15% w/w, or 0.1% w/w, or 0.05% w/w or about 0.03% w/w or about 0.01% w/w). In some embodiments, mussel lipid is used in the form of PCSO-254®, i.e mussel lipid extract containing 0.15% w/w vitamin E. In some embodiments the mussel lipid, optionally containing vitamin E, is further formulated with a carrier oil, such as olive oil. While in some embodiments the mussel lipid is a mussel lipid extract and contains added vitamin E, the addition of vitamin E is optional, and thus, in some embodiments, the mussel lipid extract is used neat, i.e., does not contain any other additional ingredients, such as vitamin E.

Mussel lipid, in various forms, may also be purchased from commercial suppliers.

Krill oil may be prepared from any suitable krill species, including *Euphausia superba* (Antarctic krill), *Euphausia pacifica* (Pacific krill), *Maganycitiphanes norvegica* (Northern krill), *Euphausia crystallorophias* (ice krill), *Euphausia frigida, Euphausia longirostris, Euphausia triacantha* and *Euphausia vallentini*. In some preferred embodiments, the krill oil is obtained from *Euphausia superba*.

Marine lipids contain fatty acids, particularly omega-3 fatty acids such as EPA and DHA, in free and triglyceride form. Similarly, krill oil is also rich in omega-3 fatty acids, however, krill oil contains significant amounts of phospholipids, where the fatty acids are attached to a phosphate head group via a glycerol moiety. It is this phospholipid bound form of the fatty acids that is more efficiently taken up into cellular membranes than the triglyceride form, and thereby more readily bioavailable. Typical phospholipids found in krill oil may include: phosphatidylcholine, alkyl acyl phosphatidylcholine, phosphatidylinositol, phosphatidylserine, lysophosphatidylcholine, lyso alkyl acyl phosphatidylcholine, phosphatidylethanolamine, alkyl acyl phosphatidylethanolamine, cardiolipin+N-acyl phosphatidylethanolamine, lysophosphatidylethanolamine, and lyso alkyl acyl phosphatidylethanolamine. Krill oil also contains appreciable amounts of astaxanthin, an antioxidant, which is also responsible for its red colour.

In some embodiments, the krill oil contains at least about 1% w/w, 5% w/w, 10% w/w, or at least about 20% w/w phospholipids. In further embodiments, the oil contains at least about 25% w/w or at least about 30% w/w, or at least about 35% w/w, or at least about 40% w/w, or at least about 45% w/w, or at least about 50% w/w, or at least about 55% w/w, or at least about 60% w/w, or at least about 65% w/w or at least about 70% w/w, or at least about 75% w/w, or at least about 80% w/w or at least about 85% w/w phospholipids, or at least about 90% w/w phospholipids, or at least about 95% w/w phospholipids, or at least about 97% w/w phospholipids, or at least about 98% w/w phospholipids, or at least about 99%, w/w phospholipids. In some embodiments, the krill oil has a phospholipid content in the range of about 40-99% w/w. In some further embodiments, the krill oil has a phospholipid content in the range of about 60-99% w/w, for example in the range of about 65-90% w/w. As referred to herein, "enriched" krill oil refers to krill oil having a phospholipid content of least about 60% w/w. Phospholipid content may be determined by any suitable means in the art, for example $^{31}P$ NMR analysis.

Methods for preparing krill oil, including krill oil enriched in phospholipids are known in the art. Typically, fresh, frozen and/or heat treated krill (e.g. *Euphasia superba* or *Euphasia pacifica*) biomass may be extracted using solvents (e.g, alcohols, such as ethanol; ketones, such as acetone; or dimethoxyethane) and/or supercritical fluid (e.g. $CO_2$). Some non-limiting exemplary processes for preparing krill oil are described in U.S. Pat. Nos. 9,028,877, 9,375,453, 6,800,299, 8,828,447, 9,150,815, 8,383,845, WO2007/123424, WO2011/050474, WO2015/104401 and WO2015/121378, the contents of which are incorporated herein by reference. Further methods are also described herein. Krill oil may also be purchased from commercial suppliers.

In some advantageous embodiments, the krill oil has a water content of about 5% w/w or less, or about 4, or 3, or 2 or 1, or 0.5% w/w, or less. In some embodiments, the krill oil has a residual extraction solvent content of about 5% w/w or less, or about 4, or 3, or 2 or 1, or 0.5% w/w, or less. In further embodiments, the krill oil has a water content of about 5% w/w or less, or about 4, or 3, or 2 or 1, or 0.5% w/w, or less, and a residual extraction solvent content of about 5% w/w or less, or about 4, or 3, or 2 or 1, or 0.5% w/w, or less. Water and solvent may be removed by any suitable means, such as very short duration or gentle heating (e.g. 30 min, or 1 hour, or 2 hours or 3 hours, at a temperature of about or less than about 60° C., or 50° C., or 40° C., and preferably such that the integrity of the constituents is not substantially compromised), nitrogen stream or lyophilisation (freeze-drying).

The inhibitory activity of the combinations against one or more inflammatory mediators such as nitrous oxide (NO), cytokines, such as interleukins, (e.g. IL-6), prostaglandins (e.g. PG-E$_2$), and TNFα, may be useful in treating one or more disorders or symptoms in a subject whereby the inhibition of one or more of such molecules is therapeutically beneficial. In particular, the combinations of the disclosure may be useful in treating excessive acute, or chronic inflammation, and/or one or more of the symptoms associated therewith, such as pain, fever, redness and swelling. In some embodiments the combinations may be useful in treating inflammation in disorders where the pathology includes an inflammatory component, and/or pain associated with such disorders. Some non-limiting examples of disorders that include an inflammatory aspect include atherosclerosis, allergy, asthma, autoimmune disease (e.g. coeliac disease, psoriasis, rheumatoid arthritis, psoriatic arthritis), fibromyalgia, gout, migraine, osteoarthritis, ulcerative colitis, cancer, impaired cognition, including Alzheimer's disease, type 2 diabetes, delayed onset muscle soreness (DOMS), Crohn's disease and ankylosing spondylitis. In some embodiments, the combinations of the disclosure may be useful in treating joint pain or improving joint mobility associated with osteoarthritis or rheumatoid arthritis. In some embodiments, the combinations of the disclosure may be useful in treating disorders in which inhibition of PGE$_2$ may be beneficial, such as rheumatoid arthritis, migraine and pain (which may be nociceptive (somatic or visceral) pain, and/or neuropathic pain).

It will be appreciated that the combinations described herein may be adapted for separate or simultaneous administration. Where adapted for simultaneous administration, the combination may be provided and/or administered as an intimate composition or a mixture which comprises both the mussel lipid extract and krill oil, or as discrete dosage forms of each combination component. Where the mussel lipid extract and krill oil are each provided and/or administered separately, they may be administered simultaneously, one after the other, or each at a different time.

In further embodiments, the mussel lipid and krill oil may optionally be formulated, either together or individually, in combination with one or more pharmaceutically acceptable carriers and/or additives. Some examples of suitable carriers are edible oils, such as olive oil, castor oil, flaxseed oil, grapeseed oil, fish oil (e.g. tuna oil), canola oil, vegetable oil, sunflower oil, chia oil, soybean oil, sesame oil, algal oil, and mixtures thereof. One or more optional additives, such as anti-oxidants, vitamins (such as fat soluble vitamins (A, D, E and K), or water soluble vitamins (B1, B2, B3, B5, B6, B7, B9, B12, C), dietary minerals, amino acids, odour and taste masking agents, emulsifiers, pharmaceutically acceptable alcohols, (e.g. ethanol, glycerol, propylene glycol, and polyethylene glycol) or other viscosity modifiers, surfactants (e.g. polysorbates), suspension agents, lactose, dextrose, sucrose, mannitol, sorbitol, glucose, lubricants, binders, starches, absorption enhancers and preservatives etc. may also be included. A carrier or additive may perform one or more functions. The mussel lipid and/or krill oil may optionally be further supplemented or combined with one or more additional purified or partially purified components of mussel and krill oil, such as, astaxanthin and esters thereof, fatty acids (e.g. EPA, DHA), either in free acid, acid ester, triglyceride or phospholipid form, sterols, sterol esters, amino acids, peptides and proteins, and glycosaminoglycans (e.g. chondroitin sulfates). Other anti-inflammatory foods, such as whole ground form, or extracts thereof, e.g. turmeric (curcumin), ginger, garlic, cloves etc., may also be optionally incorporated.

The formulated combinations may be prepared according to methods known in the art. Such methods include the step of intimately bringing the mussel lipid extract and/or krill oil into association with the carrier, optionally together with one or more additive ingredients. It will be understood that any carrier or additive will be pharmaceutically acceptable.

Thus, in some embodiments, the mussel lipid and krill oil are formulated, either separately or together, with a carrier oil, such as olive oil. In some embodiments, the carrier oil comprises from about 10% w/w to about 90% w/w, such as about 20% w/w to about 80% w/w of the combination or composition. In further embodiments, the carrier oil comprises about 25% w/w, or about 30% w/w, or about 35% w/w, or about 40% w/w, or about 45% w/w, or about 50% w/w, or about 55% w/w, or about 60% w/w, or about 65% w/w, or about 70% w/w, or about 75% w/w of the combination or composition. In some embodiments, the weight ratio of carrier oil to combined amount of mussel lipid and krill oil is about 3:1, or about 2.5:1, or about 2:1, or about 1.5:1, or about 1:1, or about 1:1.5, or about 1:2, or about 1:2.5 or about 1:3.

While any form of administration is contemplated herein, such as oral, parenteral, topical, transdermal or subdermal, advantageously, in some embodiments the combinations of the disclosure may be provided and/or administered in an oral dosage form. In some embodiments the combinations can be presented in a bulk form, for example as liquids, syrups, pastes, semi-solid waxes, dispersions, suspensions, emulsions (e.g. water-in-oil or oil-in-water), pulverised powders or microencapsulated powders, from which individual dosages can be measured. Measurement and/or administration may be by any means, such as spoon or scoop, syringe, dropper, or measuring cup. Measured dosages may be administered to the subject directly or mixed through, poured on, or sprinkled on food or beverages.

In other embodiments, the combinations are advantageously presented in unit oral dosage forms, i.e. a fixed dosage form. Some examples of suitable unit oral dosages include individually packaged ampoules, tubes, filled syringes, sachets, chews and capsules (including hard and soft gel capsules).

One example, of a suitable unit oral dosage form is a capsule, in the form of a hard or soft shell. The shell may comprise one or more of gelatin, pullulan, hypromellose, PVA copolymer, carrageenan or other saccharide component such as starch or cellulose, or mixtures thereof, and may further include colouring agents, opacifying agents, plasticizers (e.g. sorbitol, xylose, maltitol and glycerine) etc. Methods for encapsulating marine oils and lipids, such as mussel lipid and krill oil, are known in the art. See for example WO2015/121378, the contents of which are incorporated herein by reference. In some embodiments, where the krill oil is encapsulated separately, the krill oil may be encapsulated in the absence of optional additional agents, such as viscosity modifying agents, that is to say, the capsule fill consists essentially of krill oil.

In some advantageous embodiments, the mussel lipid and krill oil combinations of the disclosure are presented in soft gel capsule form, for example a soft gel capsule comprising both the mussel lipid and krill oil, or individual soft gel capsules, where the mussel lipid and krill oil are separately encapsulated, optionally together with suitable carriers and/or additives. Suitable soft gel capsules may be prepared from gelatin (or alternatively, saccharide sources such as pullulan and hypromellose), optionally with one or more plasticizers such as sorbitol and glycerine (glycerol), and additives such as colouring and opacifying agents. In one example, a soft gel capsule shell may comprise gelatin, and one or both of sorbitol and glycerine.

Microencapsulation is a method by where tiny droplets or particles are surrounded by a coating wall or are embedded in a matrix to form a powder, with the coating or matrix forming a functional barrier that avoids or reduces the propensity for chemical reactions, such as oxidation. In addition, it may provide a potential taste or odour masking role. Thus, in some embodiments, the mussel lipid and/or krill oil may be microencapsulated, either separately or together, to form a powder. Commonly used microencapsulation methods include emulsification, spray-drying, freeze-drying, co-axial electrospray, extrusion, coacervation, supercritical fluid technology, and in situ polymerization. Coating materials include natural and synthetic polymers, carbohydrates (e.g. starches, glucose), proteins (e.g. casein, gelatin) and mixtures thereof (See, for example, Bakry, A. M., et al, *Comprehensive Reviews in Food Science and Food Safety*, 15, 143, 2016, and the references cited therein, WO2014/170464 and WO2014/169315, the contents of which are included herein by reference). The mussel lipid and/or krill oil may be microencapsulated with one or more carriers or additives as described above. The microencapsulated mussel lipid and/or krill oil powder may be further encapsulated, for example in a hard shell capsule unit dosage form. The powdered microencapsulated lipid or oil may be optionally combined with one or more carriers or additives.

In some embodiments the combinations of the disclosure may be taken with food or beverages, for example by sprinkling, stirring, mixing or other means of applying or incorporating the mussel lipid extract and krill oil combination into or onto a food or beverage. Thus, the combinations may be provided in a format for incorporation into or onto a beverage or foodstuff. In some embodiments the combination, may also be formulated in the preparation of foodstuffs and beverages to provide functional foods.

In some embodiments, the mussel lipid and krill oil are formulated, either separately or together, with a carrier oil, such as olive oil, optionally with an antioxidant (e.g. vitamin E).

Subjects to be treated by the combinations of the disclosure include mammalian subjects, such as humans, primates, felines, canines, bovines, equines, porcines, leporines, ovines, and caprines, and include livestock animals (e.g. cows, horses, sheep, pigs and goats), companion animals (e.g. dogs, cats, rabbits, guinea pigs), and captive wild animals. Laboratory animals such as rabbits, mice, rats, guinea pigs and hamsters are also contemplated as they may provide a convenient test system.

Any of the dosage forms described above may be applicable for human or veterinary use as appropriate.

A treatment effective amount is intended to include an amount of the combination which, when administered according to the desired dosing regimen, is jointly effective to at least partially attain the desired therapeutic effect, including one or more of: alleviating, eliminating or reducing the duration, severity and/or frequency of inflammation and/or one or more symptoms of inflammation (e.g. heat, pain, swelling, redness), preventing or delaying the onset of, inhibiting the progression of, or halting or reversing (partially or altogether) the onset or progression of the particular disorder or condition being treated.

Suitable dosage amounts and dosing regimens can be determined by the attending physician or veterinarian, and may depend on the particular condition/symptoms being treated, the severity of the condition as well as the general age, health and weight of the subject. Suitable daily dosage amounts of the mussel lipid and/or krill oil may independently lie in the range of from about 10 mg to about 10 g, for example about 10 mg, 20 mg, 30 mg, 40 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg 1 g, 1.1 g, 1.2 g, 1.3 g, 1.4 g, 1.5 g, 1.6 g, 1.7 g, 1.8 g, 1.9 g, 2.0 g, 2.1 g, 2.2 g, 2.3 g, 2.4 g, 2.5 g, 2.6 g, 2.7 g, 2.8 g, 2.9 g, 3.0 g, 3.2 g 3.5 g, 3.7 g, 4.0 g, 4.5 g, 5.0 g, 5.5 g, 6.0 g, 6.5 g, 7.0 g, 7.5 g, 8.0 g, 8.5 g, 9.0 g, or about 9.5 g. In some further embodiments, daily dosages of the combination may lie in the range of from about 20 mg to about 15 g, for example, about 20 mg, 30 mg, 40 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg 1 g, 1.1 g, 1.2 g, 1.3 g, 1.4, g, 1.5 g, 1.6 g, 1.7 g, 1.8 g, 1.9 g, 2.0 g, 2.1 g, 2.2 g, 2.3 g, 2.4 g, 2.5 g, 2.6 g, 2.7 g, 2.8 g, 2.9 g, 3.0 g, 3.2 g 3.5 g, 3.7 g, 4.0 g, 4.5 g, 5.0 g, 5.5 g, 6.0 g, 6.5 g, 7.0 g, 7.5 g, 8.0 g, 8.5 g, 9.0 g, 9.5 g, 10.0 g, 10.5 g, 11.0 g, 11.5 g, 12.0 g, 12.5 g, 13.0 g, 13.5 g, 14.0 g, or 14.5 g.

In some embodiments, individual unit dosages (e.g. soft gel capsule) may contain about 10 mg, 20 mg, 25 mg 30 mg, 40 mg, 50 mg, 60 mg, 70 mg, 75 mg 80 mg, 90 mg, 100 mg, 110 mg, 120 mg, 125 mg, 130 mg, 140 mg, 150 mg, 160 mg, 165 mg, 170 mg, 175 mg, 180 mg, 190 mg, 200 mg, 210 mg, 220 mg, 225 mg, 230 mg, 240 mg, 250 mg, 260 mg, 265 mg, 270 mg, 275 mg, 280 mg, 290 mg, 300, mg 310 mg, 320 mg, 325 mg, 330 mg, 340 mg, 350 mg, 360 mg, 365 mg, 370 mg, 375 mg, 380 mg, 390 mg, 400, mg, 410 mg, 420 mg, 425 mg, 430 mg, 440 mg, 450 mg, 460 mg, 465 mg, 470 mg, 475 mg, 480 mg, 490 mg, or about 500 mg of the combination, optionally formulated together with a carrier oil (e.g. olive oil). In some further embodiments thereof, the combination further comprises vitamin E. In some further embodiments, thereof, the combinations comprise mussel lipid (e.g. as PCSO-524) in an amount in the range of about 10% to about 90% w/w of the total amount of total mussel lipid and krill oil, and comprise krill oil in an amount in the range of about 90% to about 10% w/w of total mussel lipid and krill oil, that is, a weight ratio of mussel lipid to krill oil of from about 10:90 to 90:10, for example, mussel lipid to krill oil in a weight ratio of about 15:85, or about 20:80, or about 25:75, or about 30:70, or about 35:65, or about 40:60, or about 45:55, or about 50:50, or about 55:45, or about 60:40, or about 65:35, or about 70:30, or about 75:25, or about 80:20, or about 85:15.

Dosages may be conveniently administered once daily, or daily dosages may be divided and administered multiple times (e.g. two, three or four times) daily. In some embodiments, the combinations of the disclosure may be administered one, two, three or more times weekly, for example on alternate days. In some embodiments, treatment may be continuous or long term, for example, over a period of at least 6-12 months or at least 2-3 years, or ongoing.

Combinations of the disclosure, for example in any one of the daily dosage amounts, may comprise mussel lipid in an amount in the range of about 1% to about 99% w/w of the total amount of total mussel lipid and krill oil, and comprise krill oil in an amount in the range of about 99% to about 1% of total mussel lipid and krill oil, that is, a weight ratio of mussel lipid to krill oil of from about 1:99 to 99:1. In some embodiments the combinations comprise mussel lipid in an amount in the range of about 5% to about 95% w/w of the total amount of total mussel lipid and krill oil, and comprise krill oil in an amount in the range of about 95% to about 5% of total mussel lipid and krill oil, that is, a weight ratio of mussel lipid to krill oil of from about 5:95 to 95:5. In some embodiments the combinations comprise mussel lipid in an amount in the range of about 10% to about 90% w/w of the total amount of total mussel lipid and krill oil, and comprise krill oil in an amount in the range of about 90% to about 10% w/w of total mussel lipid and krill oil, that is, a weight ratio of mussel lipid to krill oil of from about 10:90 to 90:10. In still further embodiments, the combinations comprise mussel lipid to krill oil in a weight ratio of about 15:85, or about 20:80, or about 25:75, or about 30:70, or about 35:65, or about 40:60, or about 45:55, or about 50:50, or about 55:45, or about 60:40, or about 65:35, or about 70:30, or about 75:25, or about 80:20, or about 85:15.

While the combinations of the disclosure may be administered as the sole anti-inflammatory therapy for any one or more disorders, they may also be administered in conjunction with an administration regimen of one or more NSAIDS, such as celecoxib, diclofenac, diflunisal, etodolac, fenoprofen, flurbiprofen, ibuprofen, indomethacin, ketoprofen, telorolac, mefenamic, meloxicam, nabumetone, naproxen, oxaprozin, piroxicam, sulindac, and tolmetin. In some embodiments, combinations of the disclosure may eliminate or reduce the potential adverse effects associated with NSAIDS, for example, by eliminating or substantially eliminating the need for additional NSAIDS therapy, or by reducing the dosage amounts and/or dosing frequency of NSAIDS required to achieve a beneficial therapeutic effect As discussed above, in one or more embodiments, the krill oil used in the combinations disclosed herein may advantageously have a phospholipid content of at least about 50% w/w, or higher, preferably at least about 60% w/w, or higher. Many prior art processes for extracting a high phospholipid (e.g. greater than about 50% or 60% w/w) krill oil from krill meal use a combination of $CO_2$ and $CO_2$/ethanol. However, it is well recognised that the higher the phospholipid content of a krill oil, the more viscous the krill oil is, with krill oils having a content of about 60% or greater typically presenting as a viscous paste at ambient temperatures. This presents manufacturing challenges, particularly on an industrial or commercial scale of oil production, as higher temperatures are required to evaporate the solvents used in the extraction process from the viscous material, with heat related damage to the oil more likely to occur. Additionally, increased pressures are then required to transfer the oil from the extraction tanks to packaging tanks.

One exemplary prior art process is described in WO2007123424. This document describes a twostep process, whereby a feed material is first extracted with pure $CO_2$ to extract out only neutral lipids (i.e. non-polar triglycerides), leaving behind a material that is, by virtue of the removal of the non-polar triglycerides, phospholipid-enriched. This phospholipid enriched material is then extracted with, $CO_2$+≥10% ethanol co-solvent to extract the polar phospholipids and remaining non-polar triglycerides together from the krill feed biomass. This method inefficiently uses plant capacity at commercial scale, as during both stages of the process much of the volume in the high pressure extractors is filled with non-extractable protein, carbohydrates and ash components in the feed biomass. It is also fundamentally a less efficient batch operation (compared to more efficient continuous operation), which may adversely impact process costs. Effectively, enrichment to deliver a final polar phospholipid content in the finished oil is achieved in the first step, directly on a bulk non-homogenous solid raw material at industrial scale. Precise prior knowledge of the polar and non-polar lipid contents of the solid feed, and how well each will subsequently extract, is required for accurate final oil enrichment. In practice, uncertainty at commercial scale may translate to costly over enrichment, which then requires final blending back to specification as required. Again this adversely impacts the economics of the process.

U.S. Pat. Nos. 9,735,453, 9,028,877, 9,320,765, and 9,072,752 describe extraction of krill with $CO_2$ or $CO_2$ plus approximately 5% ethanol to extract neutral (non-polar triglyceride) lipids, followed by $CO_2$/~20% ethanol to extract from the bulk non-homogenous solid material a krill oil with high amounts of phospholipids, astaxanthin esters and/or omega-3 fatty acids. These processes share the disadvantages described above.

The present disclosure now describes a process that, in some embodiments, may reduce, minimise or eliminate one or more of the disadvantages discussed above when preparing high, or enriched phospholipid-containing krill oil according to prior art methods, particularly on an industrial or commercial scale (e.g. when manufacturing batches of oil in the order of at least about 50, 100, 200, 300 or 500 kg and greater). Thus, the present disclosure also provides a process for preparing krill oil with a phospholipid content of at least about 50% w/w, or higher, preferably to a level of at least about 60% w/w or higher, and a process for enriching a lower phospholipid content (less than about 50% w/w) oil to a level of at least about 50% w/w or higher, preferably to a level of at least about 60% w/w or higher.

In some embodiments, the disclosure provides a 2-step process for preparing a krill oil having a phospholipid content of at least about 50% w/w wherein a first step involves extracting a first krill oil, having a phospholipid content of less than about 50% w/w from a krill biomass and then removing at least a proportion of non-polar lipid components (e.g. triglycerides) from the first krill oil to obtain a second krill oil which is enriched in phospholipids (i.e. has a higher phospholipid content) compared to the first krill oil.

In contrast to the prior art processes discussed above, some embodiments of the process commence with a non-selective extraction of oil from the krill biomass feed material. Extraction of both polar (e.g. phospholipid) and non-polar (e.g. triglyceride) lipids from solid feed meal may be achieved using a mix of $CO_2$ and ethanol (e.g. azeotropic ethanol—a water-ethanol mixture comprising about 95% ethanol).

In some preferred embodiments, a mass ratio of at least about 15% w/w or about 20% w/w ethanol in $CO_2$ may be used, for example in the range of about 17-22% w/w. In further embodiments a mass ratio of at least about 25% w/w ethanol in $CO_2$ may be used, such as least about 26% w/w ethanol, or least about 27% w/w ethanol, or least about 28% w/w ethanol, or least about 29% w/w ethanol, or least about 30% w/w ethanol in $CO_2$ is used.

In some embodiments, including any one of the other embodiments discussed in this paragraph, extraction temperatures are at or below about 60° C., such as at or below about 55° C., or at or below about 50° C., or at or below about 45° C., or at or below 40° C., or at or below 35° C., or at or below 30° C. to advantageously reduce or minimise risk of product degradation. The extraction pressure may be set to ensure super-, sub- and/or near critical conditions for the selected temperature and ratio of $CO_2$ to ethanol. In some embodiments the pressure is in the range of about 200-350 bar, such as about 250-300 bar, although higher pressures e.g. 400 bar and greater, are technically effective and may also be used. In some embodiments, the pressure value or range produces adequate solvent density to ensure extraction of the non-polar lipids does not become rate limiting for the process. In some embodiments, extraction pressure conditions may be adjusted throughout the extraction process to move between super-, sub- or near critical conditions. In some embodiments, subcritical, and/or near critical conditions are used, the conditions for which will vary depending on the $CO_2$ to ethanol binary mix ratio (or ternary mix ratio in the case of azeotropic ethanol, which also contains water). Extraction times can be determined by those skilled in the art and may depend, inter alia, on the extraction conditions and the desired economic optimisation. In some embodiments, extraction times are typically in the range of about 1-15 hours, such as about 2-10 hours, such as about 2-5 hours or about 3-6 hours, or about 4-5 hours. This in turn can depend on, inter alia, the quantity and particle size of the biomass feed material. Larger particles will permit higher solvent flow rates to be used while still retaining a static biomass and uniform solvent contact. However, a larger particle, also presents an increased diffusion requirement for the solvent to reach the centre of the particles, with more solvent being required. Thus, in some embodiments, the particle size of the feed material is, about 1-5 mm, such as about 2-3 mm.

In some further embodiments, the extraction pressure is about 300 bar and the extraction temperature is about 60° C.

Separation of the oil can be conducted at lower temperatures (e.g. about 25-35° C.) and pressures (e.g. about 25-60 bar)

The resulting extracted oil contains both polar (e.g. phospholipid) and non-polar (e.g. triglyceride) lipids, and may have a phospholipid content of less than about 50%, w/w, or less than about 45% w/w, or less than about 40% w/w, or less than about 35% w/w, or less than about 30% w/w, or less than about 25% w/w, or less than about 20% w/w, or less than about 10% w/w.

In some advantageous embodiments, water and ethanol present in the oil can then be removed using any suitable method, such as evaporation under vacuum (optionally with gentle heating, e.g., about 65° C. or less), nitrogen stream or lyophilisation. In some embodiments, the oil is subjected to evaporation under vacuum, optionally with gentle heating. This may further be followed by short residence time (e.g. 1-3 seconds) at a higher temperature, (e.g. about 70° C., about 75° C. or about 80° C.) to remove water and ethanol co-solvent from the low viscosity polar and non-polar lipid mix, the high proportion of non-polar lipids affording the low viscosity. In some preferred embodiments, temperatures advantageously do not exceed about 60° C. throughout the gentle heating under vacuum, in order to avoid or minimize degradation of the components of the extracted oil. In further embodiments, temperatures throughout the gentle heating under vacuum advantageously do not exceed about 55° C., or about 50° C. or about 45° C., or about 40° C., or about 35° C., or about 30° C., or about 25° C.

In some embodiments, the residual volatile content (water and ethanol) after evaporation is about or less than about 3% w/w, as this may minimize the possibility of residual ethanol and water adversely impacting separation of the lipids in the later enrichment step. In further embodiments, the residual volatile content is about or less than about 2.5% w/w, or about or less than about 2.0% w/w, or about or less than about 1.5% w/w, or about or less than about 1.0% w/w, or less than about 0.5% w/w, or less than about 0.3% w/w, or less than about 0.1% w/w.

At this stage, after evaporation, due to the presence of the non-polar lipid components, the oil is still fluid and can be easily analysed, e.g. for phospholipid and/or omega-3 fatty acid content. This is important as an accurate analysis is required in order to calculate desired degree of enrichment, and hence phospholipid content of the final oil achieved in the following step. In particular, where a final high phospholipid content is desired, over-enriching (i.e. further removal of non-polar lipids), even by small margins can lead to processing problems due to excessive viscosity. The evaporated oil can be thoroughly mixed to ensure homogeneity, optionally after transferral to intermediate product tanks. Optionally, the oil may be gently heated (e.g. at a temperature of less than or about 60° C. 55° C., or about 50° C. or about 45° C., or about 40° C., or about 35° C., or about 30° C., or about 25° C.) to assist in maintaining a fluid and homogeneous material for analysis. The less viscous nature of unenriched oil obtained by the first step $CO_2$/EtOH extraction compared to the first step bulk solid biomass used in the prior art processes discussed above, may, in some embodiments, advantageously allow for more accurate compositional analysis as bulk homogeneity can be more readily achieved. In some embodiments this may advantageously avoid, minimize or otherwise reduce over-enrichment of phospholipids in the subsequent selective extraction of non-polar lipids, which could otherwise result in an undesirably viscous or immovable solid product.

The second step of the process involves preferred or selective extraction of the non-polar (triglyceride) lipids from the oil obtained in the first step. If the unenriched oil obtained by the first extraction step has been transferred to intermediate tanks, it is returned to the extraction facility. The oil is further subjected to $CO_2$ extraction, in some preferred embodiments at supercritical conditions, e.g. at or greater than about 300 bar and at about 60° C., in order to selectively extract the non-polar (triglyceride) lipids. In some embodiments, the extraction can commence with a lower pressure and then be increased incrementally to the desired level (e.g. about 300 bar). The non-polar (triglyceride) lipids can be progressively extracted, thereby enriching the remaining raffinate, until the required compositional target is achieved, for example a phospholipid content of at least about 50% w/w, or at least about 55% w/w phospholipids, or at least about 60% w/w, phospholipids or at least about 65% w/w phospholipids, or at least about 70% w/w phospholipids, or at least about 75% w/w phospholipids, or at least about 80% w/w phospholipids, or at least about 85% w/w phospholipids, or at least about 90% w/w phospholipids, or at least about 95% w/w phospholipids, or at least about 97% w/w phospholipids, or at least about 98% w/w phospholipids, or at least about 99%, w/w phospholipids.

In some embodiments, once the required quantity of non-polar lipid has been extracted to achieve the desired level of phospholipid enrichment, partially depressurising the extraction vessel allows the remaining pressure to assist in discharge of the now enriched (and more viscous) raffinate as required. Draining of enriched high viscosity oil can be tolerated to a greater degree by draining from an extractor still partially pressurised. In this way, extremely viscous materials can be transferred for onwards blending and formulation.

In one or more embodiments, the process may allow for semi continuous processing, with individual extraction vessels being changed out on a continuous rotation but one at a time while other extraction vessels continue to operate. In this way, stopping to change multiple extractor batches may be avoided.

In other embodiments, the second step described herein can be used to enrich the phospholipid content of any krill oil having a phospholipid content of less than about 50%, w/w, in order to obtain a krill oil having a phospholipid content of at least about 50% w/w.

In some embodiments, the starting krill oil has a phospholipid content of about 45% w/w or less, or about 40% w/w or less, or about 35% w/w or less, or about 30% w/w or less, or about 25% w/w or less, or about 20% w/w or less, or about 10% w/w, or less. In some embodiments, the final enriched oil may have a phospholipid content of at least about 55% w/w phospholipids, or at least about 60% w/w phospholipids or at least about 65% w/w phospholipids, or at least about 70% w/w phospholipids, or at least about 75% w/w phospholipids, or at least about 80% w/w phospholipids, or at least about 85% w/w phospholipids, or at least about 90% w/w phospholipids, or at least about 95% w/w phospholipids, or at least about 97% w/w phospholipids, or at least about 98% w/w phospholipids, or at least about 99%, w/w phospholipids.

In some embodiments, the enriched krill oil has final a water content of about 5% w/w or less, or about 4, or 3, or 2 or 1, or 0.5% w/w, or less. In some embodiments, the krill oil has a residual extraction solvent content of about 5% w/w or less, or about 4, or 3, or 2 or 1, or 0.5% w/w, or less. In further embodiments, the krill oil has a water content of about 5% w/w or less, or about 4, or 3, or 2 or 1, or 0.5% w/w, or less, and a residual extraction solvent content of about 5% w/w or less, or about 4, or 3, or 2 or 1, or 0.5% w/w, or less. In still further embodiments, the enriched krill has a residual solvent (water and ethanol) content of 5% w/w or less, or about 4, or 3, or 2 or 1.5, or 1, or 0.5, or 0.3, or 0.1% w/w, or less.

In still other embodiments, the final enriched krill oil has a phospholipid content of at least about 60% w/w phospholipids, and a residual solvent content of about 3% w/w or less.

Other embodiments relating to krill oil as described herein, may also, as appropriate, apply to krill oil produced by the process of the disclosure.

The following examples are provided for the purpose of illustrating some embodiments of the disclosure and are not intended to limit the generality hereinbefore described.

EXAMPLES

Example 1—Preparation of 62% w/w Phospholipid Krill Oil

1. Extraction of Krill Oil From Krill Meal

Krill meal was extracted with $CO_2$/ethanol (feed ratio of ethanol to krill meal about 3.0-3.5:1 w/w), with an ethanol mass fraction in the range of about 17-22% w/w, at a temperature of 60° C. and a pressure of 300 bar. The ethanol/$CO_2$ stage extraction was between 10 and 15 hours in duration. The extracted oil/$CO_2$/EtOH mixture was separated at a pressure of 45 bar and 25° C.

Several batches of oil obtained by this method were blended to afford a krill oil containing both polar and non-polar components and having a phospholipid content of about 42% (see Table 1-1 below).

TABLE 1-1

$^{31}$P NMR Analysis of PL in Krill oil sample

| Phospholipid (PL) | | wt % of total PL | g/100 g sample |
|---|---|---|---|
| Phosphatidylcholine | PC | 76.0 | 32.3 |
| Alkyl acyl phosphatidylcholine | AAPC | 9.6 | 4.1 |
| Phosphatidylinositol | PI | 0.6 | 0.3 |
| Phosphatidylserine | PS | 0.3 | 0.1 |
| Lysophosphatidylcholine | LPC | 7.4 | 3.1 |
| Lyso alkyl acyl phosphatidylcholine | LAAPC | 0.5 | 0.2 |
| Phosphatidylethanolamine | PE | 1.3 | 0.5 |
| Alkyl acyl phosphatidylethanolamine | AAPE | 0.9 | 0.4 |
| Cardiolipin + N-acyl phosphatidylethanolamine | CL/NAPE | 2.6 | 1.1 |
| Lysophosphatidylethanolamine | LPE | 0.9 | 0.4 |
| Lyso alkyl acyl phosphatidylethanolamine | LAAPE | <0.1 | <0.1 |
| Total PL content | | | 42.5 |

2. Selective Extraction of Triglycerides From the Krill Oil Obtained From Step 1

5.9 kg of feed krill oil (having the composition as set out in Table 1-1 above) was loaded directly into a single 10.7 L extraction vessel (diameter of 155 mm). The feed material was extracted with $CO_2$ at a temperature of 60° C. and a pressure of 300 bar.

Extracts, containing largely triglycerides, were recovered and were significantly less viscous than the feed krill oil that was loaded into the extraction vessel.

The depressurization process of the extraction vessel was commenced once the total mass of extracted material reached 97% of the theoretical amount of material that could be extracted. The facility was depressurized at a constant ramp rate over a period of 15 minutes from 300 to 100 bar with $CO_2$ circulation continuing, although at 50% of the extraction flowrate. During this time the measured temperature at the exit to the extractor reduced from the 60° C. operating temperature to 50° C. The extractor was then further depressurized from 100 to 75 bar over a period of another 15 minutes without the pump running. Following that, the separation vessel was emptied of its contents.

While the extraction vessel was still at the processing temperature and 75 bar pressure, the vessel was emptied of its enriched krill oil contents from the base of the extractor vessel well below the raffinate surface level, thereby avoiding loss of high pressure CO2 with the raffinate oil being drained. The recovery of enriched oil took about an hour and in that time the pressure of the vessel decreased from 75 to 54 bar as the remaining CO2 in the extraction vessel expanded to occupy space previously taken up by the raffinate oil.

Once the discharge of enriched oil had ended, it was observed that some enriched krill oil remained in the extraction vessel on the distributor and bottom surface of the vessel, which was estimated to be less than 2% of the total mass of enriched oil. At commercial scale, any such remaining oil is recovered into the following krill oil batch for that extractor.

Prior to astaxanthin and phospholipid analysis, the enriched oil was heated in an oven for 55° C. for 1 hour. This allowed the sample to be sufficiently fluid for stirring to achieve a homogenous sample for analysis.

Table 1-2 summarises the mass, and phospholipid (PL) and astaxanthin (Asta) contents for the feed, extracted and enriched oils. Very little phospholipid (<1 g/100 g extract) and astaxanthin (<2 mg/100 g extract) was co-extracted. Overall, the mass of extract obtained from the enrichment process was 98% of the theoretical extract required for enrichment to 62% phospholipid.

TABLE 1-2

Summary of Phospholipid (PL) and Astaxanthin (Asta) contents

|  | Mass (g) | Mass (% of feed) | % PL (g/100 g) | PL mass (g) | PL (% of feed) | Asta (mg/100 g) | Asta mass (mg) | Asta (% of feed) |
|---|---|---|---|---|---|---|---|---|
| Feed | 5870.0 | 100 | 42.5 | 2494.8 | 100 | 21 | 1232.7 | 100 |
| Extract | 1939.0 | 33 | 1.0 | 19.4 | 0.8 | 1.7 | 32.3 | 2.6 |
| Enriched | 3835.6 | 65.3 | 62.0 | 2378.1 | 95.3 | 24 | 902.5 | 74.7 |
| Total out | 5774.6 | 98.4 |  | 2397.5 | 96.1 |  | 952.9 | 77.3 |

Tables 1-3 and 1-4 summarize the compositional content of the enriched oil

TABLE 1-3

$^{31}$P NMR Analysis of PL in Krill oil sample

| Phospholipid (PL) |  | wt % of total PL | g/100 g sample |
|---|---|---|---|
| Phosphatidylcholine | PC | 72.9 | 45.2 |
| Alkyl acyl phosphatidylcholine | AAPC | 10.0 | 6.2 |
| Phosphatidylinositol | PI | 1.3 | 0.8 |
| Phosphatidylserine | PS | 0.7 | 0.4 |
| Lysophosphatidylcholine | LPC | 7.6 | 4.7 |
| Lyso alkyl acyl phosphatidylcholine | LAAPC | 0.6 | 0.4 |
| Phosphatidylethanolamine | PE | 1.1 | 0.7 |
| Alkyl acyl phosphatidylethanolamine | AAPE | 1.3 | 0.8 |
| Cardiolipin + N-acyl phosphatidylethanolamine | CL/NAPE | 3.8 | 2.4 |
| Lysophosphatidylethanolamine | LPE | 0.5 | 0.3 |
| Lyso alkyl acyl phosphatidylethanolamine | LAAPE | 0.2 | 0.1 |
| Total PL content |  |  | 62.0 |

TABLE 1-4

GC Analysis of Fatty acids

| Fatty Acid | g/100 g sample (expressed as FFA) |
|---|---|
| 14:0 | 4.3 |
| 15:0 | 0.3 |
| 16:0 | 14.9 |
| 16:1 n-9 | 0.3 |
| 16:1 n-7 | 2.4 |
| 16:1 n-5 | 0.4 |
| i17:0 | 0.2 |
| 16:2 | 0.7 |
| 17:1 | 0.2 |
| i18:0 | 0.3 |
| 16:4 n-1 | 0.3 |
| 18:0 | 0.8 |
| 18:1 n-9 | 6.2 |
| 18:1 n-7 | 4.4 |
| 18:1 n-5 | 0.2 |
| 18:2 n-6 | 1.3 |
| 18:3 n-3 | 0.9 |
| 18:4 n-3 | 2.2 |

TABLE 1-4-continued

GC Analysis of Fatty acids

| Fatty Acid | g/100 g sample (expressed as FFA) |
|---|---|
| 20:1 n-9 | 0.5 |
| 20:1 n-7 | 0.2 |
| 20:4 n-6 | 0.3 |
| 20:4 n-3 | 0.3 |
| 20:5 n-3 (EPA) | 13.6 |
| 22:1 n-11 | 0.6 |
| 21:5 n-3 | 0.4 |
| 22:5 n-3 | 0.4 |
| 22:6 n-3 DHA | 8.2 |
| Others | 1.1 |
| Total n-3 | 26.0 |
| Total fatty acids | 66.5 |

Example 2

Mussel lipid extract was prepared according to WO97/09992 and used in the form of PCSO-524® (Pharmalink International Limited, Hong Kong). Krill oil was prepared by the process of Example 1, having the compositional content as set out in Tables 1-3 and 1-4 above.

Sample Preparation

Fresh samples were prepared daily. The samples were mixed by inversion before sampling. The samples were weighed in 1.5 mL centrifuge tubes and made to 100 mg/mL with ethanol to prepare the stock. The stock mixtures were prepared by weighing out the oils in the correct ratio and then making up to concentration with ethanol. Serial dilutions of the stock solution were made in ethanol. The serial dilutions were then diluted (1 in 100) in cell culture medium before being added to the cells (in triplicate) with a final 1 in 10 dilutions. This resulted in an ethanoic concentration of 0.1% for all doses and controls. Krill oil contained approximately 62% w/w phospholipids. Mussel lipid extract was used in the form of PCSO-524®.

The abbreviations used in presenting the results are set out in Table 2-1 below:

TABLE 2-1

| Abbreviations | |
|---|---|
| Abbreviation | Description |
| LY | PCSO-524 ® |
| Krill | Enriched Krill oil (62% PL) |
| 90% | A mixture containing 90% w/w LY and 10% w/w Krill. |
| 75% | A mixture containing 75% LY w/w and 25% w/w Krill |
| 50% | A mixture containing 50% LY w/w and 50% w/w Krill |
| Olive | Food grade olive oil |
| 1400W | CAS No 214358-33-5 |
| Dexa | Dexamethasone |
| Diclo | Diclofenac |

Assays

The anti-inflammatory activity was determined in lipopolysaccharide (LPS) and interferon γ (IFNγ)-stimulated murine macrophages, RAW264.7 cells cultured in standard cell culture media and incubated with LPS and IFNγ in the presence or absence of different test compounds/extracts and positive controls. The production of inflammatory mediators, including NO, $PGE_2$ and $LTB_4$, cytokines TNFα and IL-6, were measured by established methods using commercial kits. Each sample was tested with at least 3 concentrations (using 3 replicates, maximum concentration was 100 μg/ml) (n=9), with relevant internal controls (Table 2-2). The cytotoxicity of each sample was also determined by MTT assay. No cytotoxicity was detected for any concentration tested.

The assay parameters for each assay are summarised in Table 2-2. Briefly, to perform the anti-inflammatory assay, the cultured RAW264.7 cells were counted and plated (0.8×105 cells/well) in 96 well plates and incubated for the indicated plating time. The medium was then aspirated and replaced with fresh medium followed by the addition of the test compounds. The compounds were incubated for 1 h prior to the addition of the stimulant. The plates were then incubated for between 4-18 h and the supernatant analysed for the mediator of interest, the remaining cell viability was determined by MTT.

The positive controls were selected based on their widespread use in similar assays, including N-(3-(Aminomethyl)benzyl)acetamidine (1400W), a slow, tight binding inhibitor of inducible nitric-oxide synthase (iNOS) (Garvey, E. P., et al, *J Biol Chem*, 1997, 21:272(8):4959-63, and dexamethasone, a commonly used cytokine inhibitor. Diclofenac is a common non-steroidal anti-inflammatory agent and known inhibitor of cyclooxygenase (COX) which produces PGE2.

TABLE 2-2

| Assay Parameters | | | | | |
|---|---|---|---|---|---|
| Assay | Plating time | Stimulation | Incubation time | Kit Supplier | Control used |
| NO | 48 h | LPS (50 ng/ml) IFγ (50 units/ml) | 18 h | Griess Reagent (Cayman) | 1400W |
| TNFα | 48 h | LPS (50 ng/ml) IFγ (50 units/nil) | 18 h | Peprotech (USA) | Dexamethasone (Sigma) |
| IL-6 | 48 h | LPS (50 ng/ml) IFγ (50 units/nil) | 18 h | Peprotech (USA) | Dexamethasone (Sigma) |

TABLE 2-2-continued

| Assay Parameters | | | | | |
|---|---|---|---|---|---|
| Assay | Plating time | Stimulation | Incubation time | Kit Supplier | Control used |
| $PGE_2$ | 24 h | LPS (50 ng/ml) IFγ (50 units/nil) | 18 h | Cayman Chemical (USA) | Diclofenac (Sigma) |

Results

1. Nitric Oxide Assay

NO is a radical metabolite, which has been shown to have numerous physiological functions both as a signalling molecule and as a toxic agent in inflammation (Coleman, 2001). NO is derived from the oxidation of L-arginine by three types of nitric oxide synthases (NOS); the constitutive forms, neuronal NOS and endothelial NOS, and the inducible form, iNOS, originally described in murine macrophages (Nathan & Xie, 1994; Stuehr & Marletta, 1985). The inducible form is continually activated once expressed, and is therefore regulated at the transcription level by NF-κB, stimulated by inflammatory molecules like LPS and IFN-γ. The production of NO by iNOS experiences hours of lag time before NO is produced in much higher (nM) sustained levels (Nathan & Xie, 1994). The inducible form of NOS is most likely implicated in inflammation and due to the higher levels of NO produced it is more easily assessed in-vitro.

NO is an unusual signalling molecule. As there is no specific cell surface receptor for NO it enters cells indiscriminately, where the effect is dependent on cell type and NO concentration, thus producing a wide range of physiological responses. NO causes increased vascular permeability, vasodilatation and generation of radicals which causes tissue damage and eliminates pathogens (Guzik, Korbut, & Adamek-Guzik, 2003). These physiological changes are associated with inflammation with the increased blood flow, allowing more immune cells to enter affected tissue thereby destroying the pathogen.

The results for the NO inhibition assay are depicted in FIGS. 1A and 1B and Table 2-3

TABLE 2-3

| $IC_{50}$ for NO Inhibition | | | | | | |
|---|---|---|---|---|---|---|
| | LY | Krill | 90% LY | 75% LY | Olive Oil | 1400 W |
| $IC_{50}$ | ~107 | ~286 | 44.8 | 40.9 | Not Active | 1.6 |

2. Tumour Necrosis Factor-Alpha

TNFα is a cell signalling protein (cytokine) involved mainly in the acute phase inflammatory response. Macrophages are the major source of TNFα, although it can be released by many other cell types such as CD4+ lymphocytes, natural killer (NK) cells, neutrophils, mast cells, eosinophils, and neurons. TNFα is produced by activation of MAPK and NF-κB. It acts to increase its own production and that of other inflammatory cytokines such as interleukin-1 beta (IL-1β). TNFα induces fever, apoptotic cell death, cachexia, inflammation and inhibits tumorigenesis and viral replication. TNFα is implicated in many disease states, including, sepsis, traumatic injury, ischemia, asthma, burns, irritable bowel syndrome, Alzheimer's disease, cancer, major depression, arthritis and multiple sclerosis (Cairns, Panacek, Harken, & Banerjee, 2000; Dowlati et al., 2010; Swardfager et al., 2010).

The results for the TNFα inhibition assay are depicted in FIGS. 2A and 2B and Table 2-4.

TABLE 2-4

| | | $IC_{50}$ for TNFα Inhibition | | | |
|---|---|---|---|---|---|
| | LY | Krill | 90% LY | 75% LY | Olive Oil | Dexa |
| $IC_{50}$ | ~238.7 | ~103.3 | 89 | 57 | DNF* | 3.328e−005 |

*Did not fit mathematical model of a dose response curve

3. Interleukin-6

Like TNFα, IL-6 is considered a pro-inflammatory cytokine. IL-6 is secreted by T cells and macrophages which stimulates an immune response. IL-6 is responsible for increased production of neutrophils in bone marrow. It supports the growth of B cells and is antagonistic to differentiation of T cells into regulatory T cells. It is capable of crossing the blood-brain barrier and initiating synthesis of $PGE_2$ in the hypothalamus, thereby changing the body's temperature set point (Banks, Kastin, & Gutierrez, 1994).

The results for IL-6 inhibition assay are depicted in FIGS. 3A and 3B and Table 2-5

TABLE 2-5

| | $IC_{50}$ for IL-6 Inhibition | | | | |
|---|---|---|---|---|---|
| | LY | Krill | 90% LY | 75% LY | Olive Oil | Dexa |
| $IC_{50}$ | 22.4 | 13.4 | 11.5 | 10.4 | ~106.8 | 1.19 |

4. Prostaglandin $E_2$

Prostaglandin E2 (PGE) is one of the lipid mediators produced from arachidonic acid (AA) by the action of the enzyme cyclooxygenase (COX) and is involved in inducing pyrexia, pain sensation, and inflammation. Aspirin and non-steroidal anti-inflammatory drugs (NSAIDS) inhibit the biosynthesis of prostanoids (including $PGE_2$), resulting in anti-pyretic, analgesic, and anti-inflammatory effects (Kawahara, K., et al, 2015, and Kawabata, A., 2011).

The results are depicted in FIGS. 4A and 4B and Table 2-6.

TABLE 2-6

| | | $IC_{50}$ for PG-$E_2$ Inhibition | | | | |
|---|---|---|---|---|---|---|
| LY | Krill | 90% LY | 75% Ly | 50% LY | Diclofenac | Olive Oil |
| Not Active | Not Active | ~112 | ~118 | 55.3 | 0.12 | DNF* |

*Did not fit mathematical model of a dose response curve

Summary of Results

Mussel lipid extract and krill oil were demonstrated in this assay system at the concentrations tested to individually inhibit NO, TNFα and IL-6, but not $PGE_2$.

The combination of mussel lipid extract and krill oil was more effective than either mussel lipid extract or krill oil alone in inhibiting NO, TNFα and IL-6. In the $PGE_2$, assay, neither mussel lipid extract or krill oil alone demonstrated inhibitory activity, but in combination, demonstrated inhibition.

Example 3—Synergy

Mussel lipid extract was prepared according to WO97/09992 and used in the form of PCSO-524®. Krill oil was prepared by the process of Example 1, having the compositional content as set out in Tables 1-3 and 1-4 above.

Samples, Preparation and Combination

Stock samples of PCSO-524® and high-phospholipid krill oil were mixed by inversion before experimental sampling. The samples were weighed in 15 mL centrifuge tubes and made to 100 mg/mL with ethanol to prepare the stock. The mixtures were prepared by mixing the diluted oils in the correct ratio. Serial dilutions were made in ethanol. The serial dilutions were then diluted (1 in 100) in cell culture medium before being added to the cells (in triplicate) with a final 1 in 10 dilutions. This resulted in an ethanoic concentration of 0.1% for all doses and controls. These doses were prepared fresh daily. Table 3-1 shows the abbreviations used for each sample.

TABLE 3-1

| Sample name abbreviations | |
|---|---|
| Abbreviation | Description |
| LY | PCSO-524 ® |
| Krill | Enriched Krill oil (62% PL) |
| LY90 | A mixture containing 90% w/w LY and 10% w/w Krill. |
| LY80 | A mixture containing 80% LY w/w and 20% w/w Krill |
| LY70 | A mixture containing 70% LY w/w and 30% w/w Krill |
| LY65 | A mixture containing 65% LY w/w and 35% w/w Krill |
| LY60 | A mixture containing 60% LY w/w and 40% w/w Krill |
| LY55 | A mixture containing 55% LY w/w and 45% w/w Krill |
| LY50 | A mixture containing 50% LY w/w and 50% w/w Krill |
| LY45 | A mixture containing 45% LY w/w and 55% w/w Krill |
| LY40 | A mixture containing 40% LY w/w and 60% w/w Krill |
| LY35 | A mixture containing 35% LY w/w and 65% w/w Krill |
| LY30 | A mixture containing 30% LY w/w and 70% w/w Krill |
| LY20 | A mixture containing 20% LY w/w and 80% w/w Krill |
| LY10 | A mixture containing 10% LY w/w and 90% w/w Krill |
| Olive | Food grade olive oil |
| 1400W | CAS No 214358-33-5 |
| Dexa | Dexamethasone |
| CI | Confidence Interval |

Assays

The anti-inflammatory activity was determined in lipopolysaccharide (LPS) and interferon γ (IFNγ)-stimulated murine macrophages, RAW264.7 cells cultured in standard cell culture media (DMEM, Foetal bovine serum 5%) and incubated in the presence or absence of different test compounds/extracts and controls. The production of inflammatory mediators, including NO, cytokines TNFα and IL-6, were measured by established methods using commercial ELISA kits (suppliers listed in Table 3-2). Each sample was tested with at least 6 concentrations (using 3 replicates, maximum concentration was 100 μg/mL) (n=9), with relevant internal controls (shown in Table 3-2). The cytotoxicity of each sample tested was determined by MTT assay. There was no cytotoxicity detected for any concentration tested.

The assay parameters for each assay are summarised in Table 3-2. Briefly, for the NO, TNFα and IL-6 assays the cultured RAW264.7 cells were counted and plated ($0.8 \times 10^5$ cells/well) in 96 well plates and incubated for 48 h. The medium was then aspired and replaced with fresh medium followed by the addition of the test compounds. The compounds were incubated for 1 h prior to the addition of the stimulant. The plates were then incubated for between 18 h and the supernatant analysed for the mediator of interest, the remaining cell viability was determined by MTT.

The positive controls were selected based on their widespread use in similar assays, including N-(3-(Aminomethyl)benzyl)acetamidine (1400W), a slow, tight binding inhibitor of inducible nitric-oxide synthase (iNOS) (Garvey et al., 1997), and dexamethasone, a commonly used cytokine inhibitor.

TABLE 3-2

Anti-inflammatory assays and positive controls

| Assay | Plating time | Stimulation | Incubation time | Kit supplier | Positive Control |
|---|---|---|---|---|---|
| NO | 48 h | LPS (50 ng/ml), IFNγ (50 units/ml) | 18 h | Griess Reagent | 1400W (Cayman) |
| TNFα | 48 h | LPS (50 ng/ml), IFNγ (50 units/ml) | 18 h | Peprotech (USA) | Dexamethasone (Sigma) |
| IL-6 | 48 h | LPS (50 ng/ml), IFNγ (50 units/ml) | 18 h | Biogems (USA) | Dexamethasone (sigma) |

Synergy Calculations

Synergism is expressed as a Combination Index. The synergism combination index (CI) and isobologram IC50 weightings were calculated using Compsyn software. The dose response curve generated in Graphpad Prism was transformed into 10 points representing the curve. These 10 points were then entered into the Compsyn program that generated a curve to fit the data points. This method was preferable to closely replicate the complete dose response curve in the synergy program. The Compsyn fit curve was then used for synergy calculations. The pattern in the synergy over the range tested can be observed with an isobologram, which plots the relative contribution of each component to the activity at the IC50. There is a straight line drawn between the two drugs being blended (Biavatti, 2009). Values below the line indicate synergy, on the line is considered additive and above the line is antagonistic.

Results

1. Nitric Oxide Assay

The combinations were assayed to determine if they demonstrated synergistic inhibition on the inflammatory signalling molecule NO. The combinations were first tested in 10% increments. The most active combination observed was LY60. Further 5% increments were then tested around LY60.

The dose response curves of the tested combinations LY90-LY10 are depicted in FIGS. 5A, 5B, 6A and 6B. IC50 values for NO inhibition and Combination Index are presented in Tables 3-3 and 3-4. A combination index less than 1 indicates synergy. The isobologram for the 10% increments is depicted in FIG. 7.

TABLE 3-3

$IC_{50}$ values for NO inhibition of combinations LY90-LY10

| | LY | K | LY90 | LY80 | LY70 | LY60 | LY50 | LY40 | LY30 | LY20 | LY10 | 1400 W |
|---|---|---|---|---|---|---|---|---|---|---|---|---|
| $IC_{50}$ (μg/mL) | 204 | 265 | 105 | 109 | 74 | 67 | 83 | 85 | 111 | 125 | 134 | 25 |
| 95% CI (μg/mL) | 136 to 392 | 144 to 1108 | 87 to 136 | 88 to 144 | 63 to 90 | 59 to 77 | 64 to 117 | 68 to 115 | 81 to 183 | 98 to 194 | 98 to 248 | 21 to 32 |

TABLE 3-4

IC50s (CI) and Combination Index for NO inhibition of combinations LY75 to LY45

| | LY75 | LY70 | LY65 | LY60 | LY55 | LY50 | LY45 |
|---|---|---|---|---|---|---|---|
| $IC_{50}$ (μg/mL) | 123 | 68 | 84 | 65 | 86 | 79 | 84 |
| 95% CI for $IC_{50}$ (μg/mL) | 97 to 160 | 65 to 85 | 69 to 96 | 60 to 73 | 70 to 90 | 69 to 89 | 73 to 100 |
| Combination Index | 0.80 | 0.50 | 0.55 | 0.48 | 0.54 | 0.77 | 0.61 |

2. TNFα Assay

The combinations were assayed to determine if they demonstrated synergistic inhibition on the inflammatory cytokine TNFα. The combinations were first tested in 10% increments. The most active combination observed was LY50. Further 5% increments were then tested around LY50.

The dose response curves of the tested combinations LY90-LY10 are depicted in FIGS. 8A, 8B, 8C, 9A and 9B. IC50 values for TNFα inhibition and combination index are presented in Tables 3-5 and 3-6. A combination index less than 1 indicates synergy. The isobologram for the 10% increments is depicted in FIG. 10.

TABLE 3-5

IC50 values for TNF inhibition

| | LY | K | LY90 | LY80 | LY70 | LY60 | LY50 | LY40 | LY30 | LY20 | LY10 |
|---|---|---|---|---|---|---|---|---|---|---|---|
| IC50 | ~606 | ~966 | — | 56 | 64 | 53 | 43 | 48 | 64 | 61 | 77 |
| 95% CI | — | — | — | 49 to 67 | — to 75 | 44 to 64 | 35 to 50 | 37 to 58 | — to 71 | 39 to 90 | 56 to 134 |

*— no estimate possible

TABLE 3-6

IC50's and CI for LY70-LY35 (n = 9)

| | LY70 | LY65 | LY60 | LY55 | LY50 | LY45 | LY40 | LY35 |
|---|---|---|---|---|---|---|---|---|
| IC50 | 91 | 80 | 78 | 68 | 69 | 90 | 70 | 73 |
| 95% CI | 64 to 189 | 60 to 137 | 64 to 98 | 54 to 87 | 60 to 80 | 68 to 128 | 57 to 89 | 59 to 92 |
| Combination Index | 0.14 | 0.12 | 0.114 | 0.097 | 0.096 | 0.123 | 0.094 | 0.095 |

3. IL-6 Assay

The combinations were assayed to determine if they demonstrated synergistic inhibition on the inflammatory cytokine IL-6. The combinations were first tested in 10% increments. The most active combination observed was LY60. Further 5% increments were then tested around LY60.

The dose response curves of the tested combinations LY90-LY10 are depicted in FIGS. 11A, 11B, 12A and 12B. IC50 values for IL-6 inhibition and Combination Index are presented in Tables 3-7 and 3-8. A combination index less than 1 indicates synergy. The isobologram for the 10% increments is depicted in FIG. 13.

TABLE 3-7

IC50s for IL-6 inhibition (n = 3)

| | LY | K | LY90 | LY80 | LY70 | LY60 | LY50 | LY40 | LY30 | LY20 | LY10 | Dex |
|---|---|---|---|---|---|---|---|---|---|---|---|---|
| IC50 (µg/mL) | 173 | 114 | ~100 | 53 | 36 | 34 | 37 | 52 | 41 | 60 | ~60 | 0.010 |
| 95% CI (µg/mL) | 104 to 1311 | 92 to 191 | | 41 to 61 | 29 to 45 | 27 to 42 | 30 to 44 | 44 to 60 | 32 to 51 | 50 to 72 | | 0.004 to 0.03 |

TABLE 3-8

IC50s and Combination Index for IL-6 inhibition

| | LY70 | LY65 | LY60 | LY55 | LY50 | LY45 | LY40 | LY35 | LY30 |
|---|---|---|---|---|---|---|---|---|---|
| IC50 | 36 | 39 | 34 | 43 | 37 | 49 | 52 | 41 | 41 |
| 95% CI | 29 to 45 | 33 to 45 | 27 to 42 | 37 to — | 30 to 44 | 40 to 58 | 44 to 60 | 30 to 54 | 32 to 51 |
| Combination Index | | 0.27 | 0.23 | 0.31 | 0.27 | 0.37 | 0.4 | 0.32 | 0.32 |

Summary of Results

Mussel lipid extract and krill oil, used in combination, were demonstrated in this assay system to meet the mathematical criteria for synergy in inhibiting NO, TNFα and IL-6.

Example 4—Patient Study

Patients suffering from a variety of pain/inflammatory conditions were administered a combination of mussel lipid extract (in the form of PCSO-542) and krill oil (61% PL) in a ratio of PCSO-542 to krill oil of 75:25, in capsule form. The composition of said capsules in presented in Table 4-1.

TABLE 4-1

Composition of 150 mg oil blend capsules

| Ingredient | Weight % |
|---|---|
| Fill Component | |
| Olive oil | 66.67% |
| PCSO-542* Mussel oil (*Perna canaliculus*) | 25% (37.5 mg) |
| Krill oil* (*Euphausia superba*) | 8.33% (12.5 mg) |
| Shell Component (before drying) | |
| Gelatin (bovine) | 46.5 |
| Glycerine | 12.6 |
| Sorbtiol | 6.00 |
| water | 34.9 |

*contains 0.15% w/w vitamin E (i.e. approx. 0.056 mg/capsule)

Dosage typically ranged from 2-8 capsules per day, over one, two or three dosages. Prior to commencing treatment with the combination, patients had typically been taking one or more NSAIDS, including paracetamol or ibuprofen, to manage pain. The results are depicted in Table 4-2.

TABLE 4-2

Summary of patient results

| Patient (gender/age) | Condition | Pain level prior to treatment (1-10) | Pain level after treatment (1-10) | Other comments |
| --- | --- | --- | --- | --- |
| F, 80-84 | Severe pain in knee and shoulders | 8 | 4 | Conditions present for 3-12 years. Improvement after 2-3 weeks of treatment (2 caps per day). |
| M, 60-64 | Lumbar spine stenosis | 6-8 | 0 | Condition present for 2-3 years. Improvement after 4-5 days of treatment (6-8 caps/day). |
| M, 40-44 | Lumbar pain | 7 | 4 | Condition present for 15 years. Improvement after 7 days of treatment (3 caps/day). |
| F, 45-49 | Chronic back pain | 8 | 4-5 | Condition present for 2 years. Improvement after 2-3 weeks of treatment (3 caps/day). |
| M, 50-54 | Joint pain in hands- nerve damage/swollen knuckles | 6 | 2 | Condition present for 2 years. Improvement after 1 week of treatment (3 caps/day). |
| M, 50-54 | Chronic back pain - herniated disc | 2-8, depending on activity | 2-3 | Condition present for 25 years. Improvement after 3 days of treatment (4 caps/day). |
| F, 65-69 | Chronic knee and shoulder pain | 10 | 5 | Condition present for 5 years. Improvement after 2 weeks of treatment (4 caps/day). |
| M, 20-24 | Severe allergy - coughing, inflamed nasal passage and nasal drip | 8 | 5 | Condition present for 4 years. Improvement after 3 weeks of treatment (4 caps/day). |
| M, 40-44 | Back pain - herniated disc | 9 | 5 | Condition present for 8 years. Improvement after 3 weeks of treatment |
| F, 50-54 | Back pain | 7 | 01-1 | Condition present for 1 month. Improvement after 1 week of treatment |
| F, 55-59 | Osteoporosis - pain varies with activity | 7-8 | 1-3 | Condition present for 15 years. Improvement after 1½ weeks of treatment (4 caps/day). |
| M, 65-69 | Knee pain | 8-10 | 2-3 | Condition present for 14 years. Improvement after 1½ weeks of treatment (4 caps/day). |

TABLE 4-2-continued

Summary of patient results

| Patient (gender/age) | Condition | Pain level prior to treatment (1-10) | Pain level after treatment (1-10) | Other comments |
|---|---|---|---|---|
| M, 50-54 | Neck pain, stiff knees | 5 | 3 | Condition present for several years. Improvement after 3 weeks of treatment (3 caps/day). |
| M, 50-54 | Body aches and pain in knees and elbow post-surgery | 7-8 | 2-3 | Improvement after a few days of treatment |
| F, 65-69 | Arthritis/tendonitis in finger joints | 6 | 2 | Condition present for several months. Improvement after few days of treatment (6 caps/day). |
| F | Rheumatoid arthritis | 7 | Joint ache and pain reduced tremendously | Condition present for 10+ years. Improvement after few days of treatment (4 caps/day) |
| F, 50-54 | Lupus/fibromyalgia | 8 | 4 | Condition present for 10+ years. Improvement after 7-8 days of treatment |
| M, 30-34 | Shoulder pain, increasing after exercise | 7 | 4 | Improvement after 2 weeks of treatment (4 caps/day) |
| F | Pre-existing knee and ankle injury | 5 | 3 | Improvement after 2-3 weeks of treatment (4 caps/day) |
| M, 45-49 | Herniated discs, shoulder and hand injuries | 10 | General improvement | Condition present for several months. Improvement after 1 week of treatment (2 caps/day). |
| F, 40-44 | Knee discomfort (crunching sensation) | 4 | 0 | Condition present for several years. Improvement after 2 weeks of treatment (2 caps/day) |
| F | Joint stiffness and back pain | Varies daily | 5 Improved hand movement | Condition present for several years. Improvement after 1 weeks of treatment (2 caps/day) |
| F, 55-59 | Back pain | 6 | 4 | Condition present for a few years. Improvement after 2 weeks of treatment (3 caps/day) |
| M (elderly) | Joint pain | 6 | 2 | Condition present for several years. Improvement after 4 weeks of treatment (2 caps/day) |
| M | Shoulder and knee pain | 8 | 4 | Condition present for several years. Improvement after 1 week of treatment (2 caps/day) |
| M | Knee pain | 8 | 0 | Improvement after 1 week of treatment (4 caps/day). |
| F | Arthritis | 8 | 5 | Improvement after treatment (4 caps/day) |
| M | Arthritis | 8 | 5 | Condition present for several years. Improvement after treatment (patient noted increased |

TABLE 4-2-continued

Summary of patient results

| Patient (gender/age) | Condition | Pain level prior to treatment (1-10) | Pain level after treatment (1-10) | Other comments |
|---|---|---|---|---|
| | | | | improvement compared to use of Omega XL) (4 caps/day) |
| F | Arthritis | 6 | 3 | Improvement after treatment (patient noted increased improvement compared to use of Omega XL) (4 caps/day) |

REFERENCES

Biavatti, M. W. (2009). Synergy: an old wisdom, a new paradigm for pharmacotherapy. *Brazilian Journal of Pharmaceutical Sciences,* 45(3), 371-378.

Cairns, C. B., Panacek, E. A., Harken, A. H., & Banerjee, A. (2000). Bench to bedside: Tumor necrosis factor-alpha: From inflammation to resuscitation. *Academic Emergency Medicine,* 7(8), 930-941.

Coleman, J. W. (2001). Nitric oxide in immunity and inflammation. *Int Immunopharmacol,* 1(8), 1397-1406.

Dowlati, Y., Herrmann, N., Swardfager, W., Liu, H., Sham, L., Reim, E. K., & Lanctot, K. L. (2010). A Meta-Analysis of Cytokines in Major Depression. *Biological Psychiatry,* 67(5), 446-457. doi:10.1016/j.biopsych.2009.09.033

Garvey, E. P., Oplinger, J. A., Furfine, E. S., Kiff, R. J., Laszlo, F., Whittle, B. J. R., & Knowles, R. G. (1997). 1400W is a slow, tight binding, and highly selective inhibitor of inducible nitric-oxide synthase in vitro and in vivo. *Journal of Biological Chemistry,* 272(8), 4959-4963.

Guzik, T. J., Korbut, R., & Adamek-Guzik, T. (2003). Nitric oxide and superoxide in inflammation and immune regulation. *J Physiol Pharmacol,* 54(4), 469-487.

Kawabata, A., (2011). Prostaglandin $E_2$ and Pain—An Update. *Biol Pharm Bull,* 34(8), 1170-1173

Kawahara, K. (2015). Prostaglandin $E_2$-induced inflammation: Relevance of prostaglandin E receptors. *Biochim Biophys Acta,* 1851 (4), 414-421

Nathan, C., & Xie, Q. W. (1994). Nitric oxide synthases: roles, tolls, and controls. *Cell,* 78(6), 915-918.

Sinclair, A. J., Murphy, K. J. and Li, D. (2000) Marine lipids overview "news insights and lipid composition of Lyprinol". *Allerg Immunol (Paris)* 32(7), 261-271

Stuehr, D. J., & Marletta, M. A. (1985). Mammalian nitrate biosynthesis: mouse macrophages produce nitrite and nitrate in response to *Escherichia coli* lipopolysaccharide. *Proc Natl Acad Sci USA,* 82(22), 7738-7742.

Swardfager, W., Lanctot, K., Rothenburg, L., Wong, A., Cappell, J., & Herrmann, N. (2010). A Meta-Analysis of Cytokines in Alzheimer's Disease. *Biological Psychiatry,* 68(10), 930-941.

The invention claimed is:

1. A composition comprising mussel lipid extract and krill oil, wherein the weight ratio of mussel lipid extract to krill oil is in the range of about 5:95 to 99:1, wherein the composition is presented in an ampoule, tube, filled syringe, sachet, soft gel capsule, or hard capsule.

2. The composition according to claim 1 wherein the krill oil has a phospholipid content of at least about 40% w/w, or at least about 50% w/w, or at least about 60% w/w.

3. The composition according to claim 1 wherein the mussel lipid extract contains vitamin E.

4. The composition according to claim 1 wherein the weight ratio of mussel lipid extract to krill oil is in the range of about 5:95 to 95:5.

5. The composition according to claim 1 wherein the weight ratio of mussel lipid extract to krill oil is in the range of about 10:90 to 90:10.

6. The composition according to claim 1 wherein the weight ratio of mussel lipid extract to krill oil is about 5:95, or about 10:90, or about 15:85, or about 20:80, or about 25:75, or about 30:70, or about 35:65, or about 40:60, or about 45:55, or about 50:50, or about 55:45, or about 60:40, or about 65:35, or about 70:30, or about 75:25, or about 80:20, or about 85:15, or about 90:10, or about 95:5.

7. The composition according to claim 1, further comprising a carrier oil.

8. The composition according to claim 7 wherein the carrier oil comprises from about 10% w/w to about 90% w/w of the total composition.

9. The composition according to claim 7 wherein the weight ratio of carrier oil to combined amount of mussel lipid extract and krill oil is from about 3:1, to about 1:3.

10. The composition according to claim 1, encapsulated in a soft gel capsule.

11. The composition according to claim 1, comprising about 10 mg to about 1.0 g of mussel lipid extract.

12. The composition according to claim 1, comprising about 10 mg to about 500 mg of mussel lipid extract.

13. The composition according to claim 1, comprising about 10 mg to about 1.0 g of f krill oil.

14. The composition according to claim 1, comprising about 10 mg to about 500 mg of krill oil.

15. The composition according to claim 1, comprising about 10-500 mg of total combined amount of mussel lipid extract and krill oil.

16. The composition according to claim 1, comprising about 50-300 mg of total combined amount of mussel lipid extract and krill oil.

17. The composition according to claim 1, further comprising one or more pharmaceutically acceptable additives selected from an anti-oxidant and vitamins A, D, E and K.

18. The composition according to claim 1,
wherein the composition comprises about 10-500 mg of total amount of mussel lipid extract and krill oil;

wherein the composition optionally comprises olive oil in an amount from about 10% w/w to about 90% w/w of the total composition;

wherein the composition optionally comprises one or more additives selected from an anti-oxidant and vitamins A, D, E and K; and wherein the composition is encapsulated in a soft gel capsule.

19. A method of treating inflammation in a subject in need thereof, comprising administering to said subject a composition according to claim 1.

20. A method of treating pain in a subject in need thereof, comprising administering to said subject a composition according to claim 1.

21. A method of treating joint pain or improving joint mobility associated with osteoarthritis or rheumatoid arthritis in a subject in need thereof, comprising administering to said subject a composition according to claim 1.

* * * * *